(12) United States Patent
Medema et al.

(10) Patent No.: US 12,076,242 B2
(45) Date of Patent: *Sep. 3, 2024

(54) BIOLOGICAL CHORD REPAIR SYSTEM AND METHODS

(71) Applicant: On-X Life Technologies, Inc., Austin, TX (US)

(72) Inventors: Ryan Medema, Pflugerville, TX (US); Jeffrey Nelson, Round Rock, TX (US); Anthony Lioi, Leander, TX (US); Clyde Baker, Cedar Park, TX (US); Fletcher D. Southard, Austin, TX (US); Mark E. Seeley, Austin, TX (US)

(73) Assignee: On-X Life Technologies, Inc., Austin, TX (US)

( * ) Notice: Subject to any disclaimer, the term of this patent is extended or adjusted under 35 U.S.C. 154(b) by 306 days.

This patent is subject to a terminal disclaimer.

(21) Appl. No.: 17/234,999

(22) Filed: Apr. 20, 2021

(65) Prior Publication Data

US 2021/0236286 A1 Aug. 5, 2021

Related U.S. Application Data

(63) Continuation of application No. 16/035,326, filed on Jul. 13, 2018, now Pat. No. 10,987,219, which is a
(Continued)

(51) Int. Cl.
*A61F 2/24* (2006.01)
*A61B 17/00* (2006.01)
(Continued)

(52) U.S. Cl.
CPC ...... *A61F 2/2457* (2013.01); *A61B 17/00234* (2013.01); *A61B 17/0401* (2013.01);
(Continued)

(58) Field of Classification Search
CPC ............... A61F 2/2457; A61B 17/0401; A61B 2017/0464; A61B 17/06166; A61B 2017/0406; A61B 2017/06057
See application file for complete search history.

(56) References Cited

U.S. PATENT DOCUMENTS

| 5,340,360 | A | 8/1994 | Stefanchik |
| 5,374,278 | A | 12/1994 | Chesterfield et al. |

(Continued)

FOREIGN PATENT DOCUMENTS

| JP | 20092686832 A | 11/2009 |
| WO | 2008007243 A2 | 1/2008 |

OTHER PUBLICATIONS

International Searching Authority, "Notification of Transmittal of the International Search Report and the Written Opinion of the International Searching Authority," mailed Nov. 19, 2013, in International application No. PCT/US2013/055120.
(Continued)

*Primary Examiner* — Brian E Pellegrino
(74) *Attorney, Agent, or Firm* — Trop, Pruner & Hu, P.C.

(57) ABSTRACT

An embodiment includes a chordal replacement system comprising: a pledget coupled to a first suture length and at least one of a first needle and a first ferrule; a second suture length coupled to the pledget and at least a second needle; and a third suture length coupled to the pledget and at least a third needle; wherein the second and third suture lengths are not monolithic with each other and do not constitute a single suture. Other embodiments are described herein.

19 Claims, 29 Drawing Sheets

Related U.S. Application Data continuation of application No. 14/422,019, filed as application No. PCT/US2013/055120 on Aug. 15, 2013, now Pat. No. 10,022,224.

(60) Provisional application No. 61/684,514, filed on Aug. 17, 2012, provisional application No. 61/732,107, filed on Nov. 30, 2012, provisional application No. 61/816,386, filed on Apr. 26, 2013.

(51) Int. Cl.
*A61B 17/04* (2006.01)
*A61B 17/06* (2006.01)
*A61B 17/062* (2006.01)
*A61B 17/064* (2006.01)
*A61L 17/04* (2006.01)
*A61L 17/10* (2006.01)
*A61L 17/12* (2006.01)

(52) U.S. Cl.
CPC .... *A61B 17/06166* (2013.01); *A61B 17/0625* (2013.01); *A61B 17/064* (2013.01); *A61L 17/04* (2013.01); *A61L 17/10* (2013.01); *A61L 17/12* (2013.01); *A61B 2017/00243* (2013.01); *A61B 2017/00526* (2013.01); *A61B 2017/0406* (2013.01); *A61B 2017/0419* (2013.01); *A61B 2017/0464* (2013.01); *A61B 17/06004* (2013.01); *A61B 2017/06057* (2013.01); *A61B 2017/0649* (2013.01); *A61L 2430/34* (2013.01)

(56) References Cited

U.S. PATENT DOCUMENTS

| | | | |
|---|---|---|---|
| 5,643,295 | A | 7/1997 | Yoon |
| 6,610,071 | B1 | 8/2003 | Cohn et al. |
| 6,629,534 | B1 | 10/2003 | St. Goar et al. |
| 7,083,636 | B2 | 8/2006 | Kortenbach |
| 7,635,386 | B1 | 12/2009 | Gammie |
| 8,439,969 | B2 | 5/2013 | Gillinov et al. |
| 9,480,562 | B2 | 11/2016 | Gillinov et al. |
| 10,022,224 | B2 | 7/2018 | Medema et al. |
| 10,987,219 | B2 * | 4/2021 | Medema ............ A61B 17/0401 606/232 |
| 2003/0078653 | A1 | 4/2003 | Vesely et al. |
| 2003/0105519 | A1 | 6/2003 | Fasol et al. |
| 2004/0122512 | A1 | 6/2004 | Navia et al. |
| 2004/0122513 | A1 | 6/2004 | Navia et al. |
| 2004/0143323 | A1 | 7/2004 | Chawla |
| 2004/0210303 | A1 | 10/2004 | Sedransk |
| 2005/0075727 | A1 | 4/2005 | Wheatley |
| 2006/0195182 | A1 | 8/2006 | Navia et al. |
| 2006/0195183 | A1 | 8/2006 | Navia et al. |
| 2006/0259135 | A1 | 8/2006 | Navia et al. |
| 2006/0287716 | A1 | 12/2006 | Banbury et al. |
| 2007/0118151 | A1 | 5/2007 | Davidson |
| 2007/0118154 | A1 | 5/2007 | Crabtree |
| 2007/0135843 | A1 | 6/2007 | Burkhart |
| 2007/0239275 | A1 | 10/2007 | Willobee |
| 2008/0065203 | A1 | 3/2008 | Khalapyan |
| 2008/0140095 | A1 | 6/2008 | Smith et al. |
| 2008/0149685 | A1 | 6/2008 | Smith et al. |
| 2008/0195126 | A1 | 8/2008 | Solem |
| 2009/0005863 | A1 | 1/2009 | Goetz et al. |
| 2009/0088837 | A1 | 4/2009 | Gillinov et al. |
| 2010/0249919 | A1 | 9/2010 | Gillinov et al. |
| 2010/0298935 | A1 | 11/2010 | Melvin et al. |
| 2011/0202002 | A1 | 8/2011 | Gordon et al. |
| 2011/0288635 | A1 | 11/2011 | Miller et al. |
| 2012/0046693 | A1 | 2/2012 | Denham et al. |
| 2012/0143215 | A1 | 6/2012 | Corrao et al. |
| 2016/0278919 | A1 | 9/2016 | Gillinov et al. |

OTHER PUBLICATIONS

Cagli, K., "A Simple Method of Making Artificial Chordal Loops for Mitral Valve Repair," The Society of Thoracic Surgeons, 2010, vol. 89, pages e12-e14.

Kobayashi, J., "Ten-Year Experience of Chordal Replacement With Expanded Polytetrafluoroethylene in Mitral Valve Repair," Circulation, 2000, vol. 102, pp. III 30-34.

Rankin, S.J., "Adjustable Artificial Chordal Replacement for Repair of Mitral Valve Prolapse," The Society of Thoracic Surgeons, 2006, vol. 81, pp. 1526-1528.

Gillinov, Marc, et al., "Pre-Measured Artificial Chordae for Mitral Valve Repair," The Annals of Thoracic Surgery, 2007, pp. 2127-2131.

San Tec, "Implant Chordae Loop," Santec surgical sutures for cardiovascular and general surgery brochure, downloaded Oct. 15, 2015, 2 pages.

Von Oppell, U. O., et al., "Chordal Replacement for Both Minimally Invasive and Conventional Mitral Valve Surgery Using Premeasured Gore-Tex Loops," The Society of Thoracic Surgeons, 2000, 3 pages.

European Patent Office, Office Action mailed Jun. 24, 2016 in European Patent Application No. 13829525.8 (8 pages).

European Patent Office, Office Action mailed Sep. 28, 2017 in European Patent Application No. 13829525.8 (4 pages).

* cited by examiner

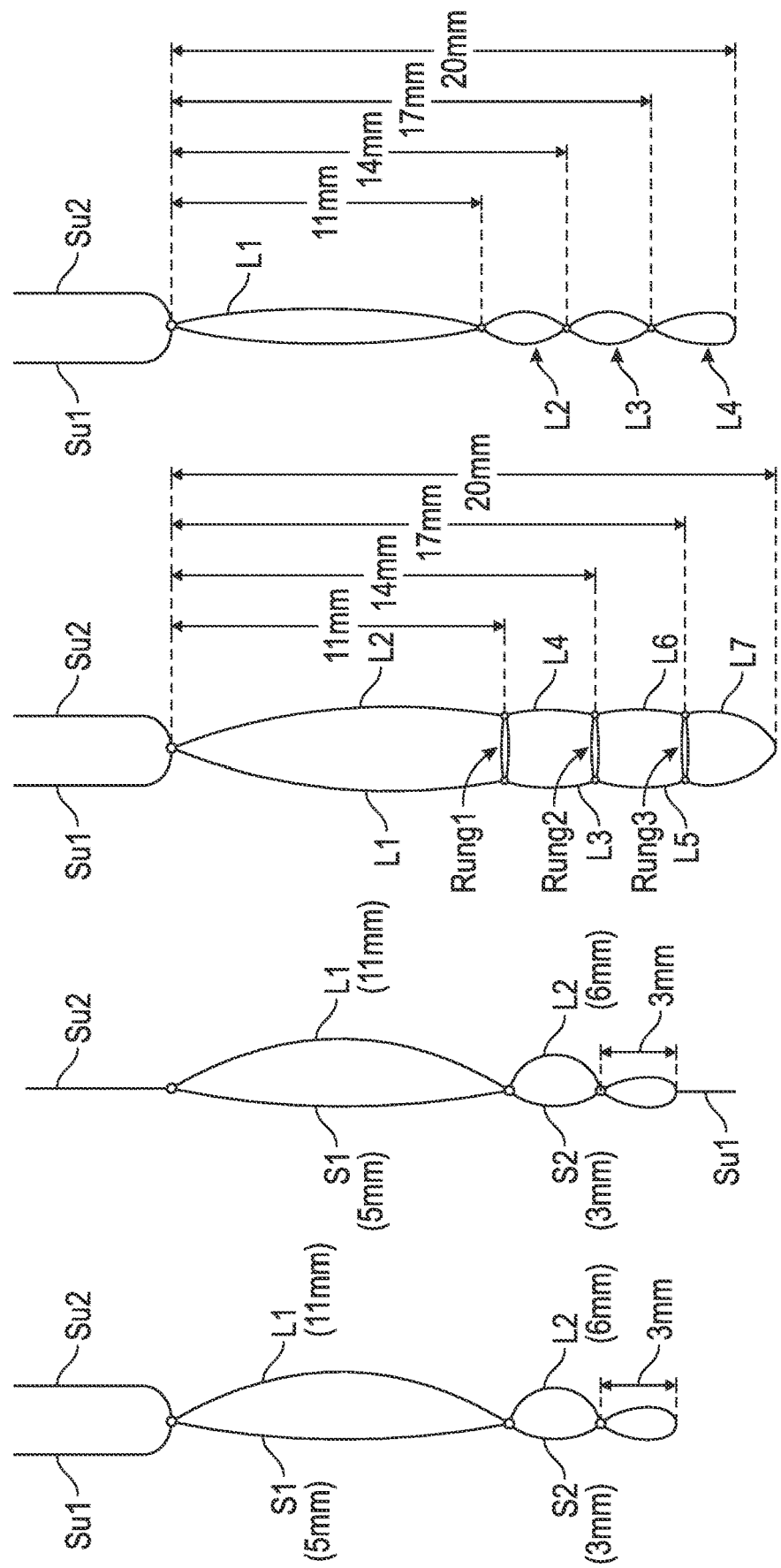

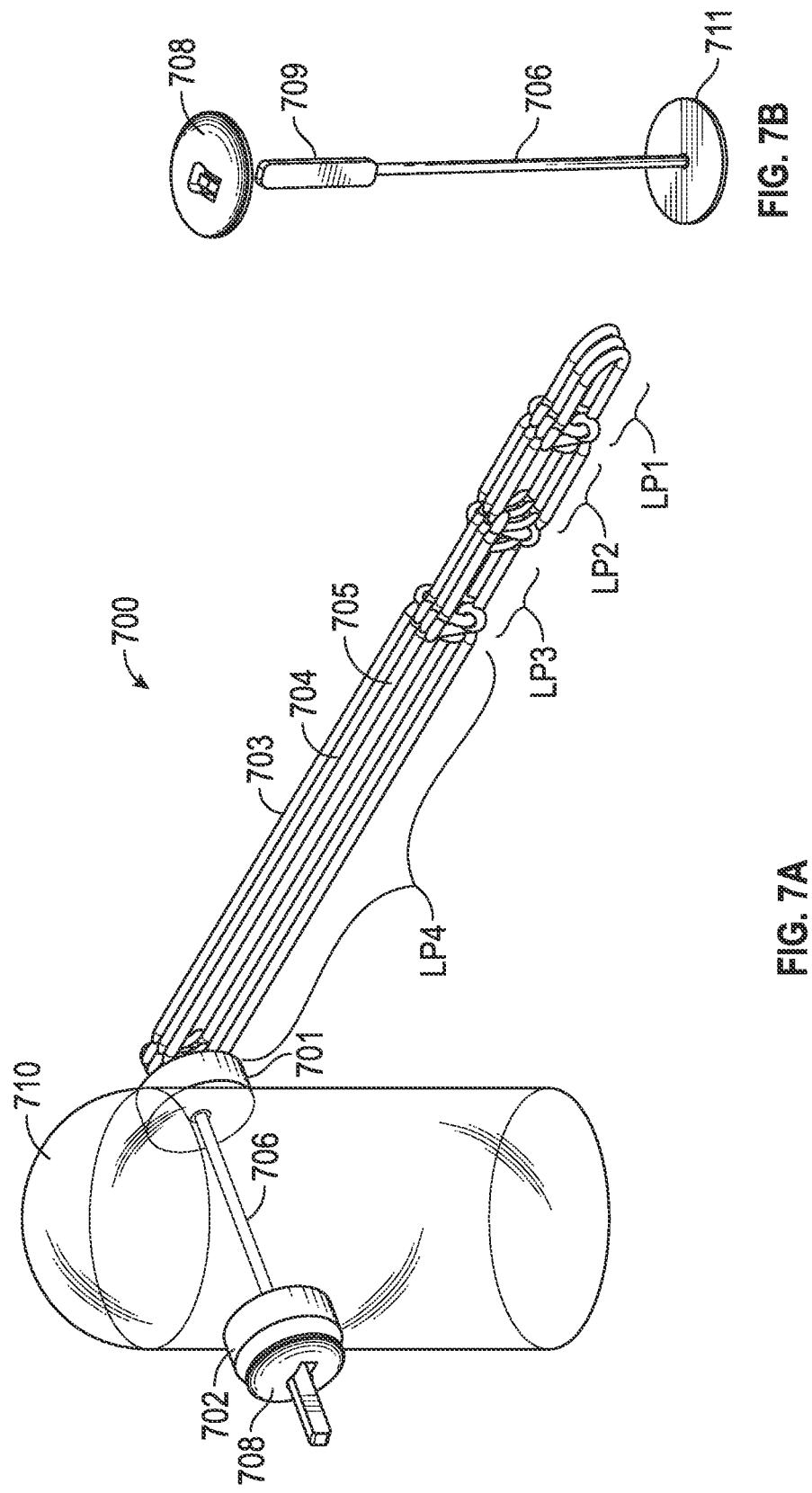

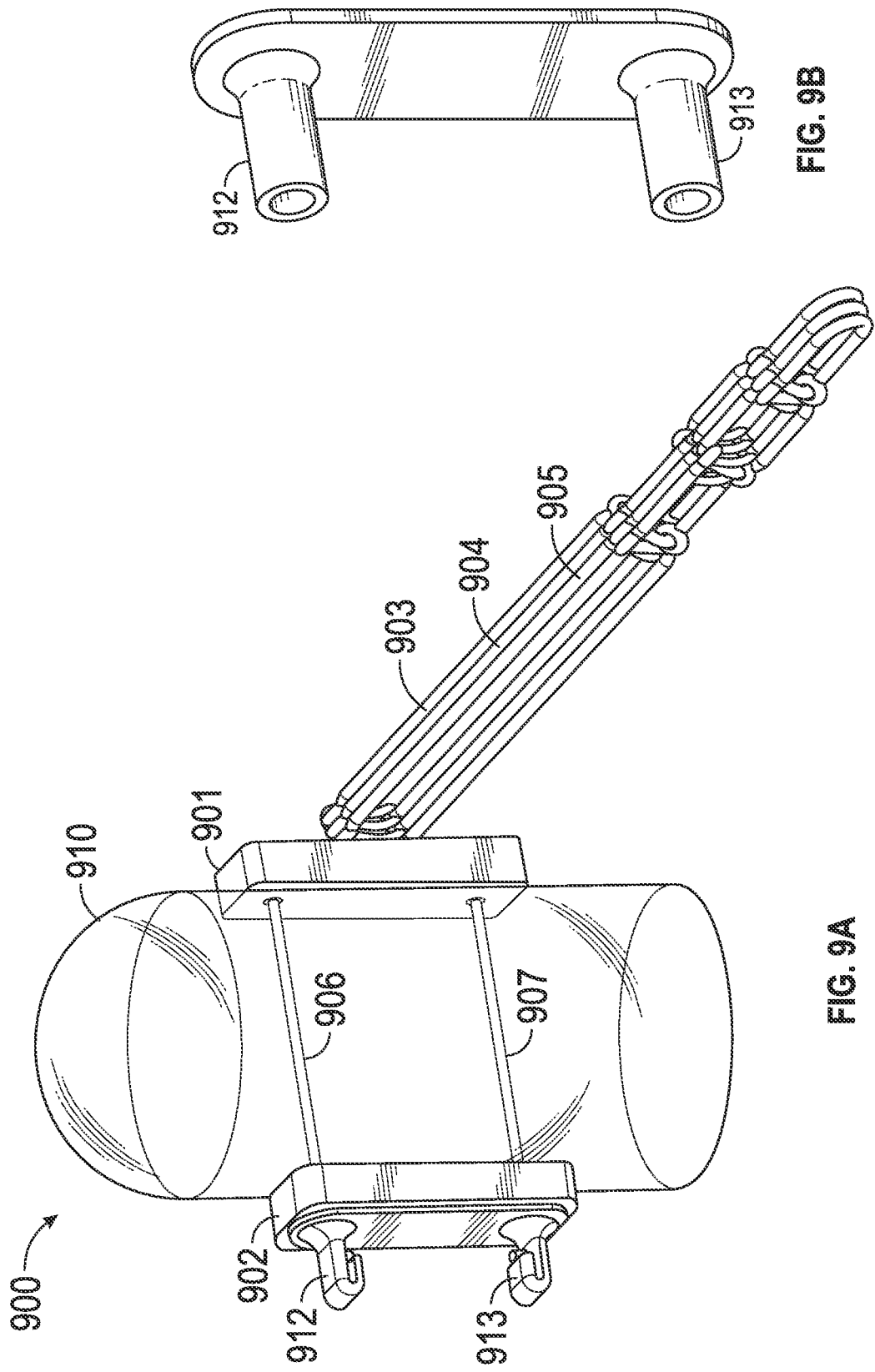

Step 1

Step 2

Step 3

Step 4

Step 5

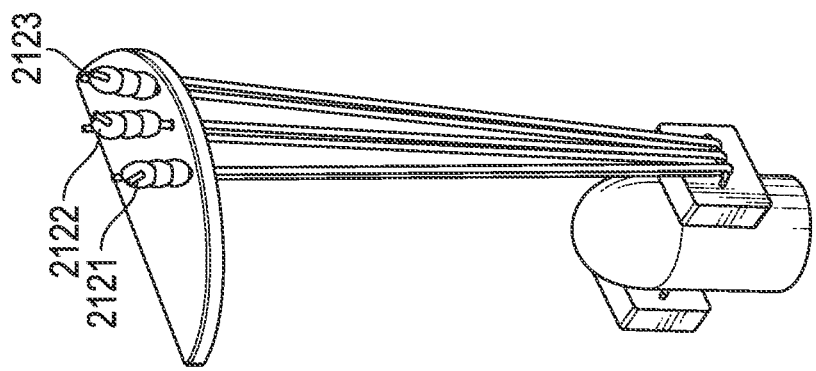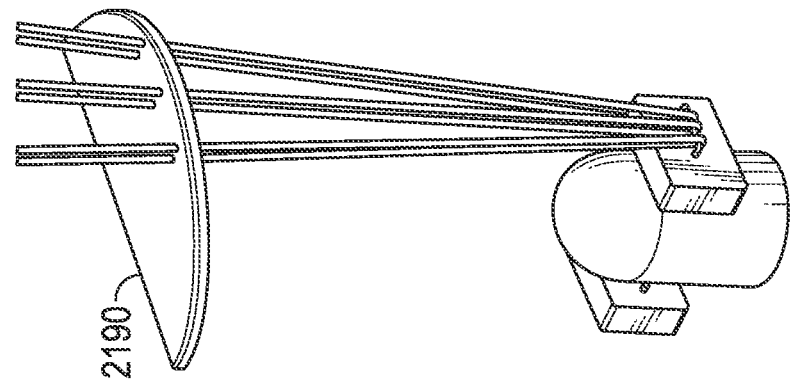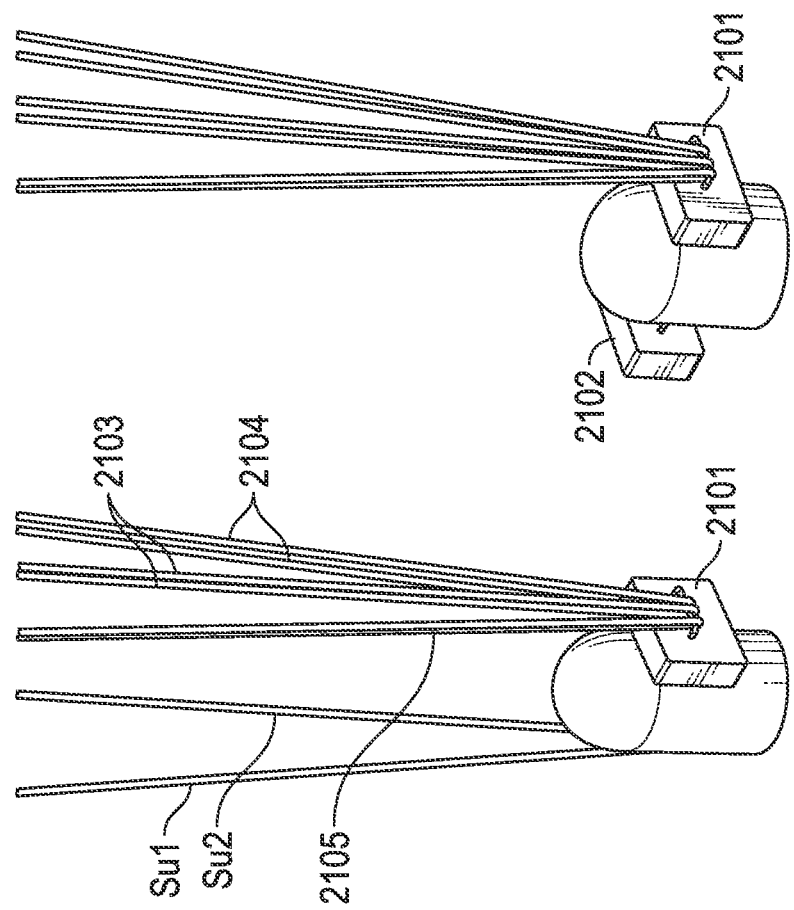

BIOLOGICAL CHORD REPAIR SYSTEM AND METHODS

CLAIM OF PRIORITY

This application is a continuation of U.S. patent application Ser. No. 16/035,326, filed Jul. 13, 2018 and entitled "Biological Chord Repair System and Methods", which is a continuation of U.S. patent application Ser. No. 14/422,019, filed Feb. 17, 2015, granted as U.S. Pat. No. 10,022,224, issued on Jul. 17, 2018 and entitled "Biological Chord Repair System and Methods", which is a § 371 National Stage Entry of International Application No. PCT/US2013/055120, filed Aug. 15, 2013 and entitled "Biological Chord Repair System and Methods", which claims priority to: (a) U.S. Provisional Patent Application No. 61/816,386, filed Apr. 26, 2013 and entitled "Knotless Artificial Chordae Replacement"; (b) U.S. Provisional Patent Application No. 61/732,107, filed Nov. 30, 2012 and entitled "Chord and Tissue Repair Systems and Methods"; and (c) U.S. Provisional Patent Application No. 61/684,514, filed Aug. 17, 2012 and entitled "Laddered Coupling System". The content of each of the above applications is hereby incorporated by reference.

BACKGROUND

Mitral valve prolapse is a significant cause of cardiovascular morbidity and mortality. As a result, surgical intervention is often required. As one of the surgical options currently available, mitral valve repair is well established and is applicable in patients with mitral valve prolapse due to degenerative mitral-valve disease. The techniques of mitral valve repair include inserting a cloth-covered ring around the valve to bring the leaflets into contact with each other (annuloplasty), removal of redundant/loose segments of the leaflets (quadrangular resection), and re-suspension of the leaflets with artificial chordae (chordal replacement).

Regarding re-suspension, replacement of diseased mitral valve chordae with expanded polytetrafluoroethylene (ePTFE) sutures is an established technique with good long-term results. Various techniques have been described to assist the surgeon to establish the correct replacement chordal length. Despite the surgical challenges of attaching the ePTFE suture to papillary muscles and determining the correct length for artificial chordae, few effective products have been developed to assist surgeons with this challenging procedure. In general, surgical approaches have centered on individual surgeon-based techniques including the use of a small tourniquet or weaving the suture through the leaflet to the mitral annulus and thereafter readjusting the length while the ventricle is filled under pressure. These varying techniques lead to inconsistencies and varying levels of clinical success.

BRIEF DESCRIPTION OF THE DRAWINGS

Features and advantages of embodiments of the present invention will become apparent from the appended claims, the following detailed description of one or more example embodiments, and the corresponding figures, in which:

FIGS. 1-4 depict chord replacements in four embodiments of the invention.

FIGS. 6, 7A, 7B, 8A, 8B, 9A, 9B, and 10 depict multi-chord replacement systems in various embodiments of the invention.

FIG. 11 includes an embodiment of a tool for applying the various embodiments of FIGS. 6, 7A, 7B, 8A, 8B, 9A, 9B, and 10.

FIGS. 21, 22A, 22B, 22C, and 22D depict a knotless chord replacement system.

DETAILED DESCRIPTION

Figure 5A:
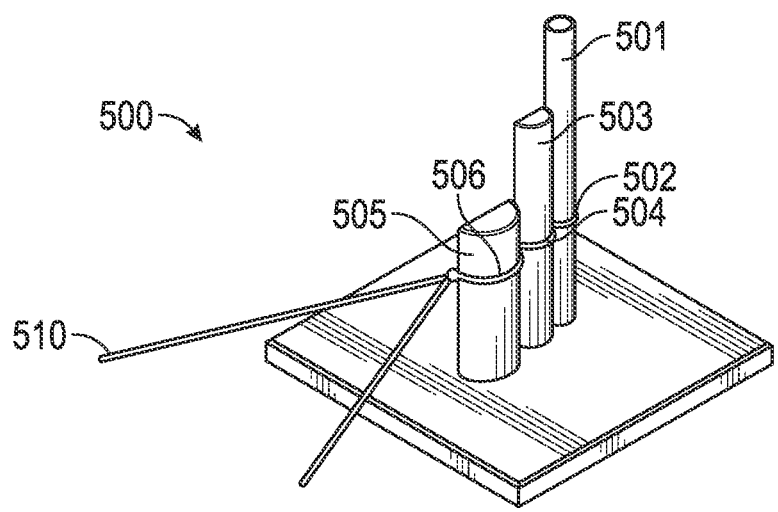
FIGS. 5A, 5B, and 5C depict a method for forming a chord replacement in an embodiment of the invention.

In the following description, numerous specific details are set forth but embodiments of the invention may be practiced without these specific details. Well-known circuits, structures and techniques have not been shown in detail to avoid obscuring an understanding of this description. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner. "Connected" may indicate elements are in direct physical or electrical contact with each other and "coupled" may indicate elements co-operate or interact with each other, but they may or may not be in direct physical or electrical contact. Also, while similar or same numbers may be used to designate same or similar parts in different figures, doing so does not mean all figures including similar or same numbers constitute a single or same embodiment.

An embodiment includes an adjustable artificial replacement chordae device/system for mitral valve repair. More specifically, an embodiment provides adjustable artificial replacement chordae that allow for variable chordal lengths encountered during valve repair surgery (e.g., mitral valve repair surgery). Such an embodiment allows for a more consistent and simple deployment of replacement chordae.

An embodiment allows for adjustment of the artificial chordae once surgically attached to the papillary muscle. The mechanisms of the embodiment are simple in that the surgeon is able to make adjustments simply by severing appropriate structures within the device which, as a result of the severing, extend the chordal length a prescribed amount. This contrasts with techniques where the surgeon must manually implant the device, check for proper length, adjust and repeat until proper coaptation has been achieved.

Embodiments of FIGS. 1-4 (see below) allow the surgeon to adjust the length of the artificial chordae in a way that is both repeatable and easier than the current manual sewing techniques.

The embodiment of FIG. 1 includes a distal loop ("loop") with length of 3 mm in a fairly relaxed state (as shown in FIG. 1). However, if the two opposing arms of the loop are brought together such that the long axis of the loop is at its maximum then the length may be greater than 3 mm. The embodiment further includes a "fine adjustment" loop with two opposing arms: the S2 and L2 segments. S2 is 3 mm and L2 is 6 mm. Thus, the two opposing arms (S2 and L2) are unequal to one another. The embodiment further includes a "gross adjustment" loop with two opposing arms: the S1 and L1 segments. S1 is 5 mm and L1 is 11 mm. As is the case with the distal loop, the dimensions for S1, L1, S2, L2 are for those arms, segments, portions, and/or lengths in the fairly relaxed state shown in FIG. 1 and those lengths may extend an amount if the arms are pulled taught (e.g., S2 may extend from 3 mm to 3.5 mm).

The proximal end of the gross adjustment loop couples to two suture lengths Su1, Su2 that may each terminate in a needle or ferrule (not shown). The surgeon may then suture the two suture lengths to papillary muscle (or any other anchoring location the surgeon chooses such as, for example, the ventricular wall).

The three knots illustrated in FIG. 1 are secure and stationary (i.e., they are fixed and do not allow sliding of arms that connect to the knot) so cutting one arm, such as arm L2, still results in a structurally secure overall suture because S2 is still secured by distal and proximal stationary knots despite L2 being cut and possibly removed so that very little of L2 still exists in the suture system.

As can be seen in FIG. 1, a surgeon may fine tune the length of the artificial cord by clipping or cutting various loop arms (or not cutting any of the loop arms). In the configuration shown for FIG. 1, a configuration is shown as follows: LOOP (3 mm)+S2 (3 mm)+S1 (5 mm)=11 mm. Members L1 and L2 may be left alone (where they will be slack due to the presence of S1 and S2) or clipped away. In other words, because the shorter arms are retained (S1 and S2) those shorter arms dictate the length and the respective longer arms (L1 and L2) do not dictate length of the suture.

Other combinations are possible as shown in FIG. 1. For example, a suture system including S1 (5 mm)+L2 (6 mm)+LOOP (3 mm) results in respective length of 14 mm, L1 (11 mm)+S2 (3 mm)+LOOP (3 mm) results in respective length of 17 mm, and L1 (11 mm)+L2 (6 mm)+LOOP (3 mm) results in respective length of 20 mm.

In several embodiments, the distal loop is retained and attached to, for example, the valve area. For example, the surgeon may suture the loop to a valve leaflet. In such an embodiment the "connection point" remains the distal loop, such as the most distal portion of the distal loop, despite the length of the overall suture length being adjustable. However, in other embodiments the surgeon may chose to remove the distal loop or a portion of the distal loop.

The embodiment of FIG. 2 is similar to the embodiment of FIG. 1 in that it includes arms S1, S2, L1, L2 that can be arranged in various combinations resulting in respective lengths of 11 mm (S1+S2+Loop), 14 mm (S1+L2+Loop), 17 mm (L1+S2+Loop), and 20 mm (L1+L2+Loop). However, the proximal coupling segment (i.e., the 3 mm loop) includes a single suture Su1, coupled to a needle (not shown), for fixation to the papillary muscle (or elsewhere). Also, the distal loop includes a suture member Su2, coupled to a needle (not shown), for fixation to a leaflet or other portion of the valve/valve area. Again, the knots of FIG. 2 (like the embodiment of FIG. 1) are secure and stationary so removing or cutting one arm (entirely or partially such that some portion remains) does not destabilize the overall integrity of the suture system. In FIG. 2 cutting S1, S2, L1, and/or L2 adjusts the chord length without moving the connection point away from the "loop" on the distal end of the suture system. The same is true for the configuration of FIG. 1. In another embodiment, instead of a segment coupling to a needle the segment may couple to a ferrule (which may mate with a needle), a clip, cinch or other coupling member to couple the system to tissue, a medical device, and the like.

The embodiment of FIG. 3 includes rungs "Rung 1", "Rung 2", and "Rung 3" among 4 loops. Like FIGS. 1-2, the system of FIG. 3 may be constructed from a single monolithic suture portion. There are various connection points for coupling the system to the valve (e.g., leaflet). For example, without clipping any portion of the system the connection point is located at the distal end of the device providing a length of 20 mm. However, the distal most portions may be removed so the system is coupled to the valve at Rung 3 to provide a 17 mm suture system. Furthermore, suture systems of 14 and 11 mm are possible by respectively removing Rung 3 and Rung 2. Similar to the embodiment of FIG. 1, the embodiment of FIG. 3 includes two proximal suture ends Su1, Su2 for fixation to the heart (e.g., papillary muscle) or elsewhere. In an embodiment the surgeon can lengthen beyond 20 mm by cutting alternating lengths L1, L4, L5 and relying on lengths L2, Rung 1, L3, Rung 2, L6, Rung 3, L7 (i.e., the use of the rungs provides even greater "granularity" in terms of chord lengths options). In another embodiment a single suture strand may be used for Su1, Su2, L1, L2, L3, L4, L5, L6I and L7, and then the cross members rung 1, rung 2, rung 3 could be formed from separate suture strands.

The embodiment of FIG. 4 includes a series of unequally sized loops. In this example two suture members Su1, Su2 (for papillary muscle fixation) couple to a large proximal loop L1 followed by three equally sized loops L2, L3, L4. The surgeon may choose to remove zero loops for a 20 mm suture system. However, the surgeon may remove the distal most loop L4 to achieve a 17 mm system length, the two most distal loops L3, L4 to achieve a 14 mm system length, or all three distal loops L2, L3, L4 to obtain an 11 mm system length. Like the embodiment of FIG. 1, the embodiment of FIG. 4 includes two proximal suture members Su1, Su2 to couple the suture system to papillary muscle or elsewhere. Again, as addressed above, a 17 mm system length achieved when removing the distal most loop provides a 17 mm system length in the fairly relaxed configuration shown in FIG. 4. However, pulling the system taught may extend beyond 17 mm.

With the various embodiments of FIGS. 1-4, a surgeon may couple suture to the system at any location depending on his or her choice. In other words, the embodiment of FIG. 1 (with no portions removed) may be coupled to the valve at the distal most portion of the distal loop (as described above) or may be coupled at a more proximal location even though no portion is removed (e.g., at the middle knot). In such a situation the surgeon provides an additional suture at the distal most portion of the distal loop at a second location of the valve or heart.

Various embodiments, such as those of FIGS. 1-4, have been described in conjunction with mitral valve repair but other uses are possible such as tricuspid valve repair or even suturing in locations apart from the heart. For example, there are orthopedic applications such as suturing connective tissue to bone. Specifically, a surgeon may anchor a loose ligament or tendon using an embodiment of the system. One end of the system is secured to the free end of the ligament, while the other is anchored in the bone. Based on range of motion desired in the joint, the surgeon then cuts prosthetic segments (e.g., loop arms) to achieve the correct length of tendon and the appropriate range of motion. In such a case the system may constitute a general anchoring or connective prosthesis.

Also, various lengths are provided for embodiments of FIGS. 1-4 for ease of explanation. For example, the embodiment of FIG. 1 is described with lengths as follows: distal loop is 3 mm, S2 is 3 mm, L2 is 6 mm, S1 is 5 mm, and L1 is 11 mm. However, other lengths and combinations are possible in other embodiments. For example, one such embodiment includes a distal loop of 4 mm, S1 of 6 mm, L1 of 10 mm, S2 of 4 mm, and L2 of 6 mm, although many other combinations are possible. Furthermore, embodiments such as the embodiments of FIGS. 1 and 2 include 3 loops but other embodiments may include 2, 4, 5, 6, 7, 8, 9 or more loops.

In one embodiment various systems are coupled together. For example, 3 instances of the embodiment of FIG. 1 may have each of their proximal ends attached to a single pledget such that, by securing the single pledget to papillary muscles or elsewhere, the surgeon has quickly attached 3 systems to the heart. The surgeon may then "edit" each of the 3 instances to couple 3 lengths (all unequal to each other) to 3 different areas of the valve.

In one embodiment, an instance of the embodiment of FIG. 1 and an instance of the embodiment of FIG. 3 and/or the embodiment of FIG. 4 may have each of their proximal ends attached to a single pledget such that, by securing the single pledget to papillary muscles or elsewhere, the surgeon has quickly attached multiple suture systems to the heart. The surgeon may then "edit" each of the instances to couple various lengths (all unequal to each other or possibly equal to each other) to different areas of the valve.

One embodiment includes a system similar to, for example, the embodiment of FIG. 1 only the "Gross Adjustment" loop includes 3 arms instead of 2 arms. For example, the Gross Adjustment loop may include 51 (5 mm), L1 (7 mm), X1 (11 mm) to provide the surgeon more length options. Other embodiments may include 4, 5, or 6 arms per loop. Further, the 3 or more arms are not restricted to any particular loop and may be included in the "Fine Adjustment" loop in addition or instead of the "Gross Adjustment" and any other loops that are included in the system (e.g., a fourth or fifth loop).

In addition, materials are not restricted to ePTFE and may include, for example, PTFE, silk, nylon, biodegradable materials (e.g., for suturing that is temporary in nature such as is the case with some orthopedic procedures) such as polyglycolic Acid (PGA), polylactic acid (PLA), poly(lactic-co-glycolic acid) (PLGA), polydioxanone (PDS), poly (orthoester) (POE), polycaprolactone (PCL), polymethylmethacrylate (PMMA), copolymer blends of the above, and the like. Other embodiments may include biological tissue for chord lengths. Also, the system need not be limited to just one material. For example, in the embodiment of FIG. 2 the S1 arm may include ePTFE and the L1 arm may include PTFE to supply the surgeon with length options and, for example, elasticity options, handling options, and the like. Also, the connection locations (e.g., the distal loop and the proximal suture lengths of the embodiment of FIG. 1) may include different materials than say, for example, the S2 arm.

An embodiment uses a coupling mechanism other than a knot (or in addition to a knot where a knot is used in one loop and another coupling mechanism is used elsewhere in the system). For example, a system may include a crimped or crushed portion that holds the arms of a loop in place (such that one arm of the loop may be removed without affecting the stability of the other arm or arms of the loop), pre-tied knot bundles that cinch around the suture, a collet mechanism, and the like.

Figure 5B:
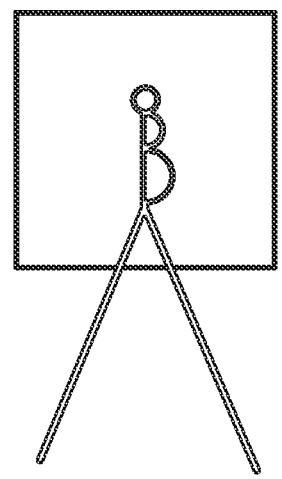
Figure 5C:
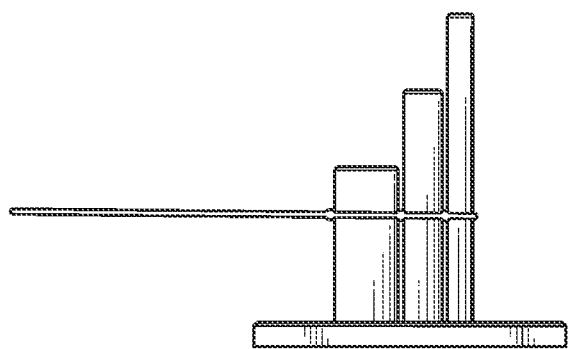

An embodiment includes a method of manufacturing a suture system. For example, the embodiment of FIGS. 5A, 5B and 5C includes an embodiment for manufacturing a suture system. The method shown in FIGS. 5A, 5B and 5C includes a member 501 with a circle cross-section for the distal loop 502 and other members including "D" shaped members 503, 505 for creating loops 504, 506 with unequal length arms (e.g., "gross adjustment" and "fine adjustment" loops). FIG. 5A shows a perspective view of the system 500 and suture system 510 while FIG. 5B and FIG. 5C—respectively show top and side views of the same. For illustration purposes in FIG. 5A, FIG. 5B and FIG. 5C—the sutures are truncated, needles are not shown, and knots are simplified.

A first example of the "looped ladder" includes a suture system comprising: a first loop including first and second knot coupled to each other by first and second segments; and a second loop including the second knot and a third knot coupled to each other by third and fourth segments; wherein the first and second loops, the first, second, and third knots, and the first, second, third, and fourth segments are all constructed from a single monolithic suture; wherein the first and second segments have unequal lengths and the third and fourth segments have unequal lengths.

A second example of the "looped ladder" system includes the subject matter of the first example of the "looped ladder" system wherein none of the first, second, third, and fourth segments have equal lengths.

A third example of the "looped ladder" system includes the subject matter of the 1-2 examples of the "looped ladder" system wherein a fifth segment connects directly to the first knot at one end of the fifth segment and couples to a needle at another end of the fifth segment.

A fourth example of the "looped ladder" system includes the subject matter of the 1-3 examples of the "looped ladder" system wherein the fifth segment is constructed from the single monolithic suture.

A fifth example of the "looped ladder" system includes the subject matter of the first example of the "looped ladder" system including a fifth segment directly connected to the first and second knots, wherein the first, second, and fifth segments all have unequal lengths.

A sixth example of the "looped ladder" system includes the subject matter of the first example of the "looped ladder" system wherein the system is configured so severing one of the first, second, third, and fourth segments does not generally weaken the structural integrity of the remaining segments.

A seventh example of the "looped ladder" system includes the subject matter of the first example of the "looped ladder" system wherein the system is configured so severing the first segment results in the system having a first overall length and severing the second segment results in the system having a second overall length unequal to the first overall length.

An embodiment includes a suture system including a first loop having a first diameter coupled to a second loop having a second diameter that is unequal to the first diameter, the first loop including two knots forming two unequal arms of different lengths, and the second loop including one of the two knots and a third knot unequal in length to the one of the two knots.

Figure 6:
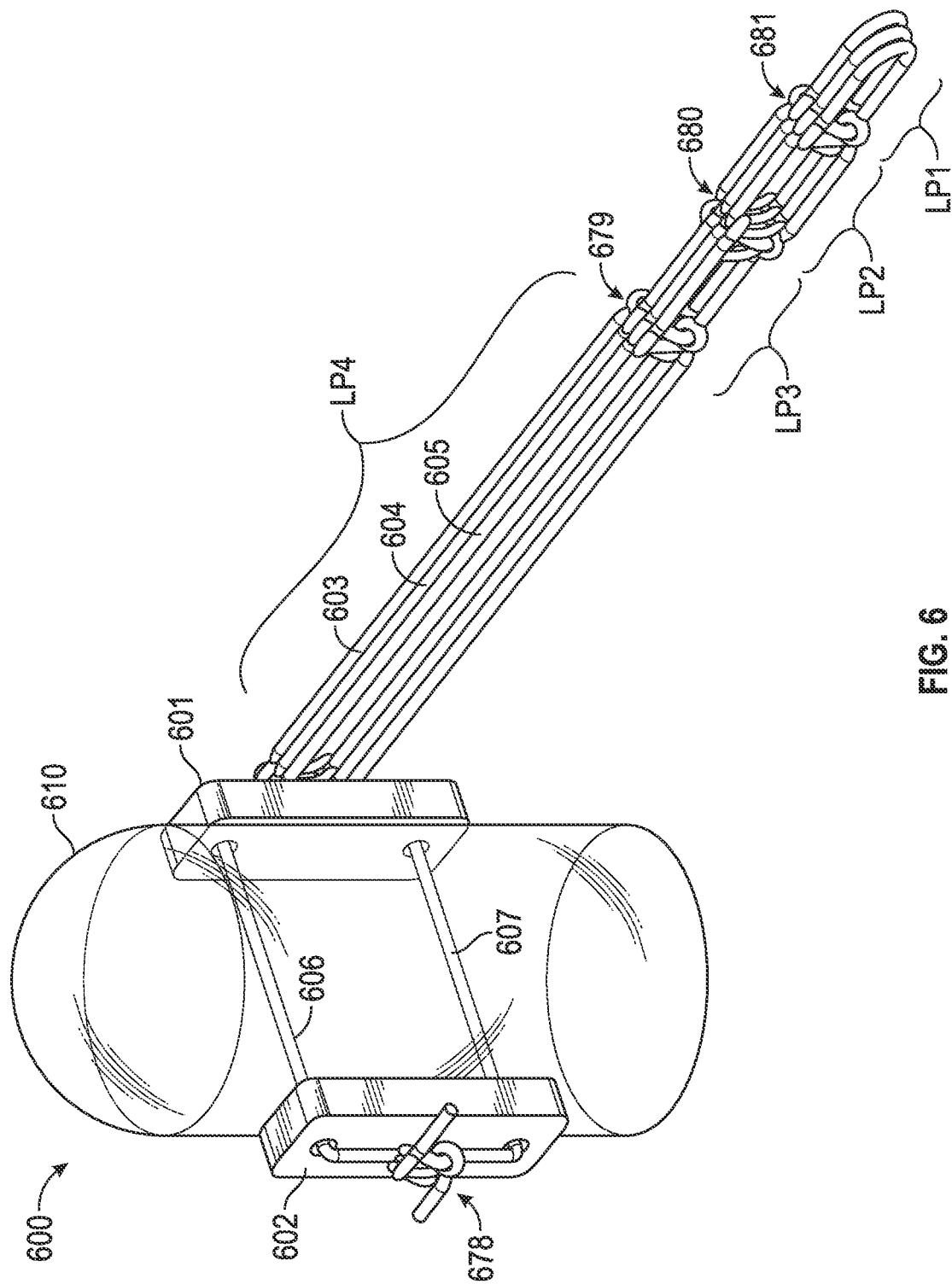

FIG. 6 includes a chord replacement system in an embodiment. System 600 includes pledgets 601, 602 through which suture members 606, 607 pass. Suture members 606, 607 adjoin one another via "7 throw square knot" 678 or any other knot the surgeon determines is suitable to secure the system to tissue (e.g., papillary muscle 610). Such a knot may be made by the surgeon using knot pushers and other known techniques conventionally employed by physicians. Loop members 603, 604, 605 may couple to pledget 601 via additional suture or any other coupler (e.g., adhesive, a bolt that passes through a loop in each of loop members 603, 604, 605 and then affixes to a nut on an opposite side of pledget 601, and the like). Each of loop members 603, 604, 605 may have multiple distal loops that may attach to tissue (e.g., valve leaflet) and may be trimmed to adjust chord length as described above with regard to FIG. 1, FIG. 2, FIG. 3, FIG. 4, FIG. 5A, FIG. 5B and FIG. 5C. In such an instance knots 679, 680, 681 may be fixed such that trimming one member, such as loop LP1 of chord 605, will not unravel or destabilize loops LP2, LP3, and LP4 of chord 605 (or similar loops for any of chords 603, 604). As mentioned above with regard to FIG. 1, FIG. 2, FIG. 3, FIG. 4, FIG. 5A, FIG. 5B and FIG. 5C, a loop such as LP4 need not have equal length arms and may include members analogous to L1 and S1 of FIG. 1 (i.e., differently sized arms of a loop that afford granularity in overall chord length).

FIG. 7A and FIG. 7B include a chord replacement system in an embodiment. System 700 includes pledgets 701, 702 through which suture member 706 passes. Member 706 couples to over-molded member 709, which couples to member 708 (in a "zip tie" or "cable tie" manner) via pledget 702 to secure system 700 to tissue 710. Chord members 703, 704, 705 (or more or less loop members in other embodiments) may couple to pledget 701 via additional suture or any other coupler (e.g., a loop affixed to member 711). In another embodiment chord members 703, 704, 705 have loop member LP4 fastened about member 706 between member 711 and pledget 701. Each of chord members 703, 704, 705 may have multiple distal loops that may attach to tissue (e.g., valve leaflet) and may be trimmed to adjust chord length as described above with regard to FIG. 1, FIG. 2, FIG. 3, FIG. 4, FIG. 5A, FIG. 5B and FIG. 5C.

Figure 8B:
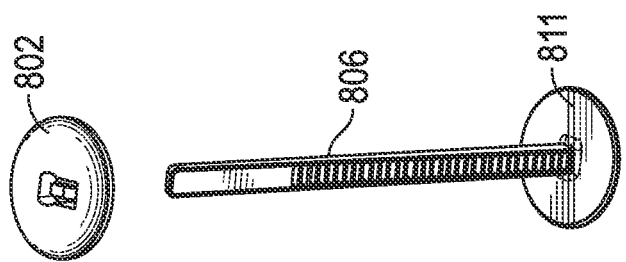
Figure 8A:
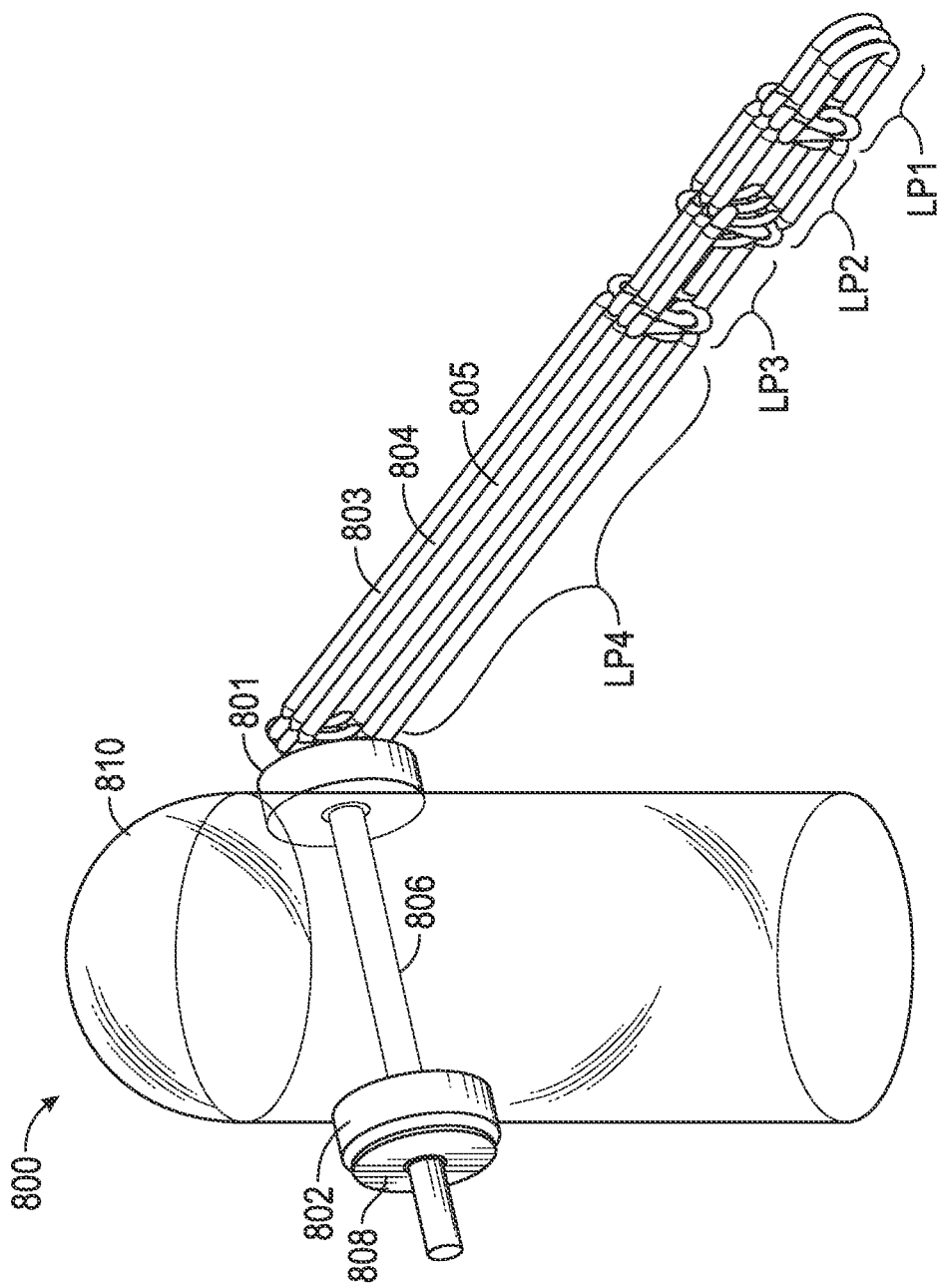

FIG. 8A and FIG. 8B include a chord replacement system in an embodiment. System 800 includes pledgets 801, 802 through which injection molded member 806 passes. Member 806 couples to through pledget 802 to receptacle 808 (e.g., in a "zip tie" manner) to secure system 800 to tissue 810. Chord members 803, 804, 805 (or more or less loop members in other embodiments) may couple to pledget 801 via additional suture or any other coupler (e.g., a loop affixed to member 811). In another embodiment chord members 803, 804, 805 have loop member LP4 fastened about member 806 between member 811 and pledget 801. Each of chord members 803, 804, 805 may have multiple distal loops that may attach to tissue (e.g., valve leaflet) and may be trimmed to adjust chord length as described above with regard to FIG. 1, FIG. 2, FIG. 3, FIG. 4, FIG. 5A, FIG. 5B and FIG. 5C.

FIG. 9A and FIG. 9B include a chord replacement system in an embodiment. System 900 includes pledgets 901, 902 through which suture member 906, 907 pass. Members 906, 907 couple through pledget 902 to receptacles 912, 913, which may be crimped (as shown) to secure system 900 to tissue 910. Chord members 903, 904, 905 (or more or less loop members in other embodiments) may couple to pledget 901 via additional suture or any other coupler (e.g., a loop affixed to member 901). Each of chord members 903, 904, 905 may have multiple distal loops that may attach to tissue (e.g., valve leaflet) and may be trimmed to adjust chord length as described above with regard to FIG. 1, FIG. 2, FIG. 3, FIG. 4, FIG. 5A, FIG. 5B and FIG. 5C.

Figures 10, 11:
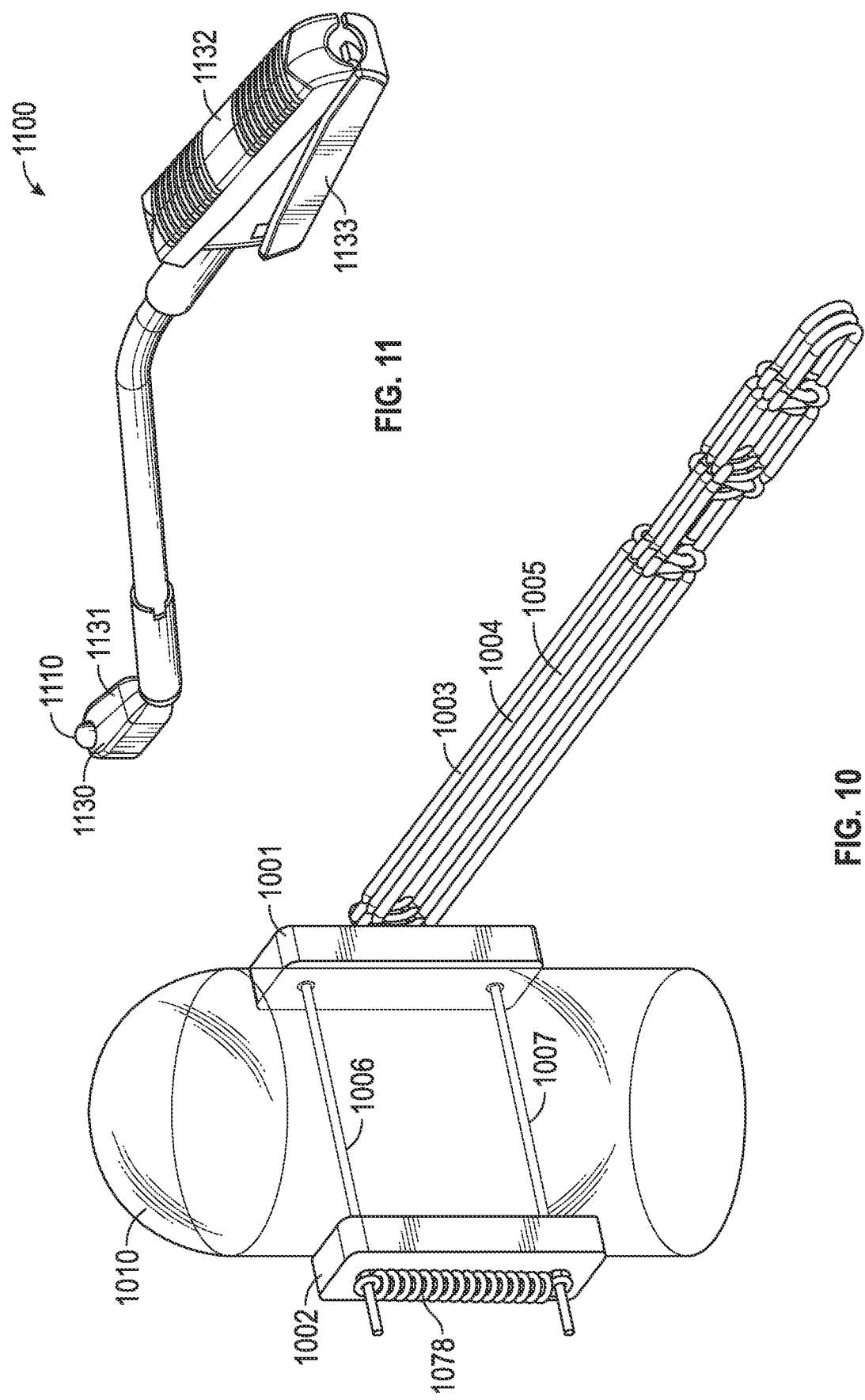

FIG. 10 includes a system similar to that of FIG. 6 only knot 1078 is a cinch knot that secures suture members 1006, 1007 through tissue 1010 and to pledget 1002. Suture members 1006, 1007 may be tied to one another or otherwise secured using securing techniques (e.g., adhesive) known to medical providers.

FIG. 11 includes tool 1100, which has clamping members 1130, 1131 to grasp tissue 1110 (e.g., papillary muscle) to then deploy securing members (e.g., needles coupled to suture, ferrules coupled to suture) through the tissue and between pledgets as shown in FIG. 6, FIG. 7A, FIG. 7B, FIG. 8A, FIG. 8B, FIG. 9A, FIG. 9B, and FIG. 10. The force applied to the tissue is regulated by the force applied to members 1132, 133.

FIG. 12A, FIG. 12B, FIG. 13A, FIG. 13B, and FIG. 13C include a chord repair system. Such systems may be provided in kits including various systems having loops of varying length that the physician can choose from according to each patient's anatomic needs. In one embodiment the "octopus" is formed by knots 1231, 1232, 1233, 1234 (e.g., half hitch knots, surgeon's end loop knot, and the like) in a straight segment of ePTFE suture resulting in loops 1203, 1204, 1205, 1206 each having a fixed length. Four of these loops are combined with a fifth straight segment of suture (which has portions Su1 and Su2 that couple together after passing through pledget 1201 (e.g., PTFE pledget) to form the uninstalled prosthetic (however in other embodiments 1, 2, 3, 5, 6, 7 or more loops may be included in the system). Since the loops are at a fixed length, a range of sizes are offered in kits and the surgeon implants the size based on some measurement of the native anatomy.

However, in another embodiment knots 1231, 1232, 1233, 1234 are adjustable knots (e.g., slip knots) that provide non-fixed length loops 1203, 1204, 1205, 1206. Such systems allow the physician to modify the chord length to accommodate each patient's anatomic needs. In an embodiment the "adjustable octopus" is similar to the "octopus" described immediately above but knots 1231, 1232, 1233, 1234 are overhanded slip knots that allow for adjustability of the prosthetic length. This is advantageous as the adjustment can be made completely out of the heart, the surgeon never/rarely needs to measure for proper chord length, and the surgeon rarely needs to go back into the ventricle and adjust the chord length. Further, almost any chord length is possible. Embodiments include a system than is adjustable among, for example, lengths of 16.5 mm, 16.65 mm, and the like in whatever lengths the surgeon wants. This is in contrast to other methods that are somewhat adjustable but have preset gradations that limited the implant flexibility.

These pre-tied prosthetic systems (whether they are fixed knot or adjustable knot embodiments), such as ePTFE systems, replace the time consuming method of hand tying prosthetics during mitral valve repair surgery from ordinary suture. The loops 1203, 1204, 1205, 1206 in the prosthetic are a fixed or variable length (depending on the type of knot used for knots 1231, 1232, 1233, 1234) and are independent of each other (so that one or more loops may be removed without affecting the other loops or the overall construction of the system). Suture segments Su1 and Su2 (and attached needle segments 1298, 1299 (see FIG. 12A used to secure the prosthetic to the valve leaflet) are integrated into the construct. Such embodiments save the surgeon time as no longer will it be necessary for the surgeon to hand tie the prosthetic or to open additional suture packages and work them through the tied prosthetic. Also, the loops are created in a more uniform manner than the surgeon may be able to accomplish on his own.

Figure 13A:
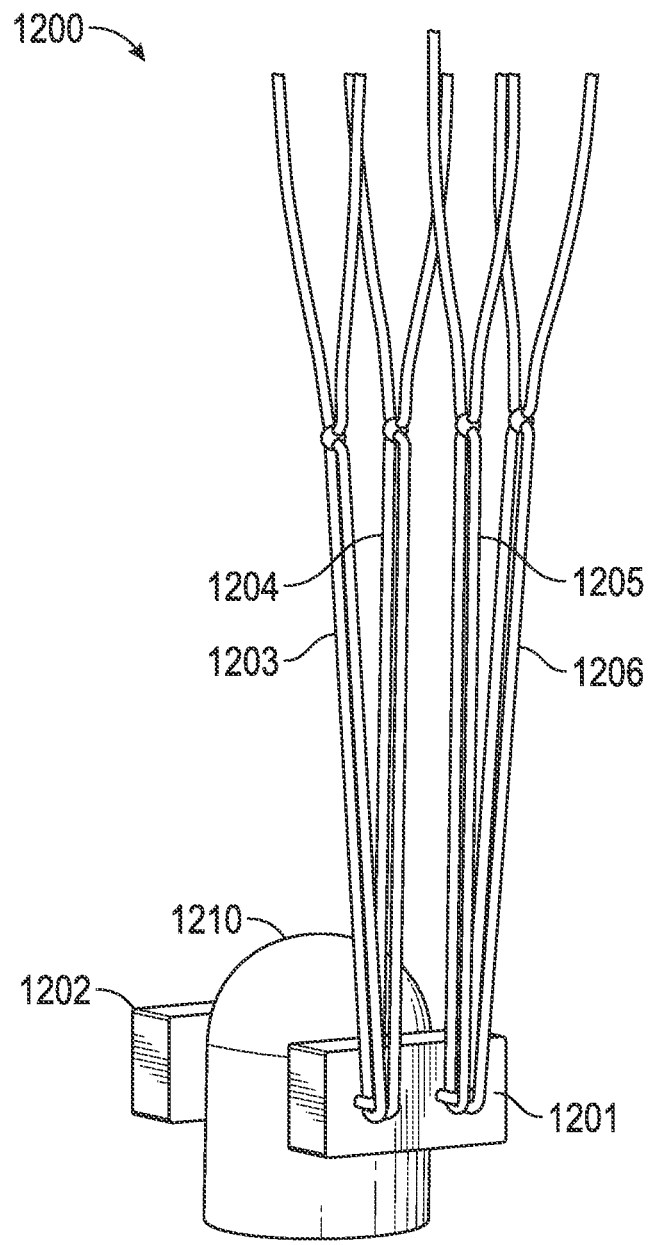
Figure 13B:
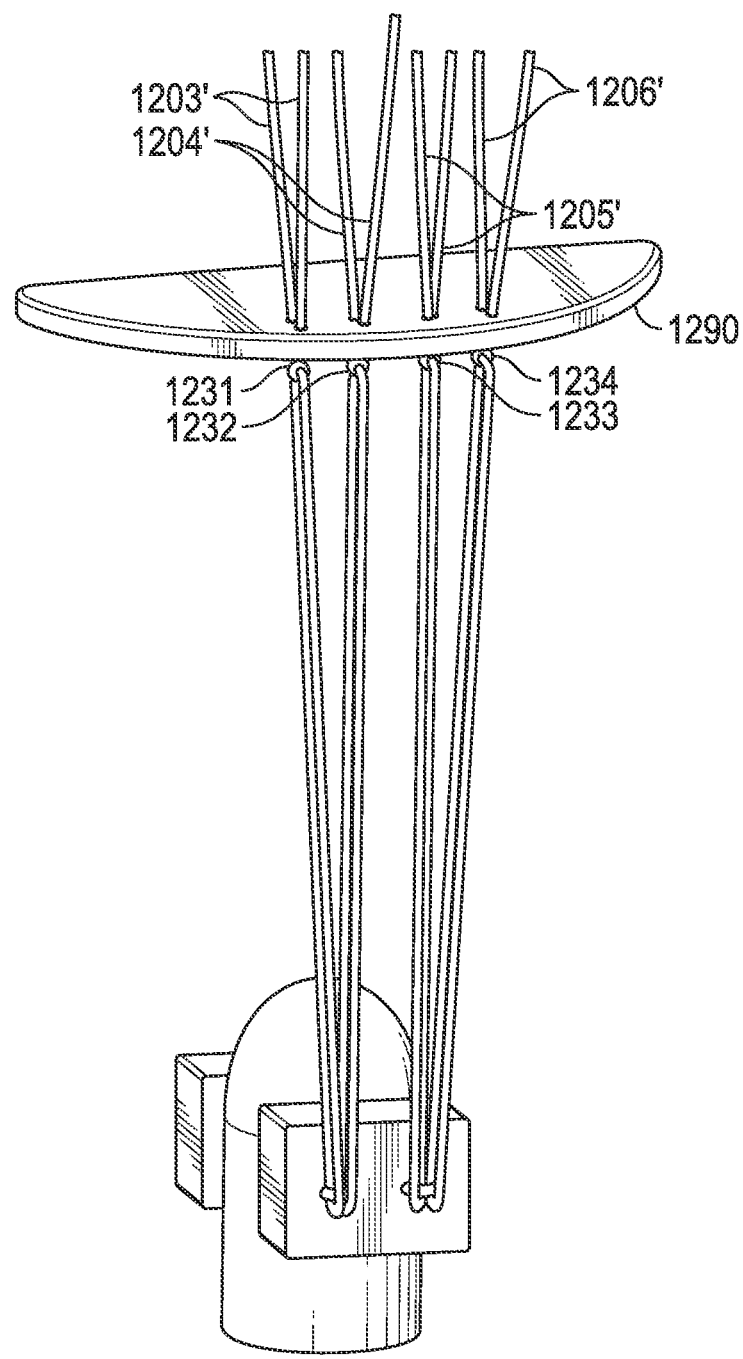
Figure 13C:
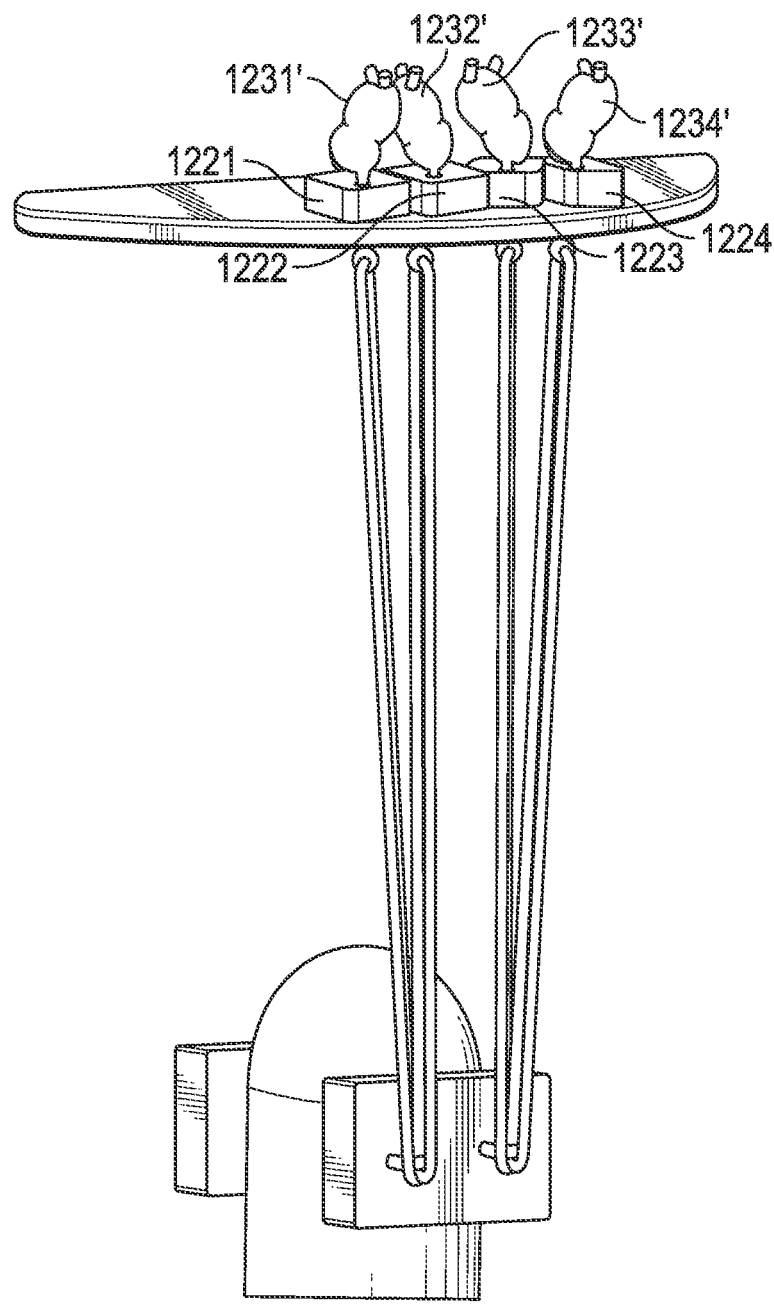

As seen in FIG. 13A, 13B, 13C, after suture lengths Su1 and Su2 couple pledgets 1201, 1202 to tissue 1210 (and suture lengths Su1 and Su2 are coupled to one another, after passing through pledget 1202, via a knot, cinching mechanism, or any other securing member), extensions 1203', 1204', 1205', 1206' pass through tissue 1290 (e.g., valve leaflet) using needles 1291 attached to extensions 1203', 1204', 1205', 1206'. Thus, in one embodiment each loop, such as loop 1203, has a knot 1231, and two extensions 1203' that each has a needle at its respective end. Extensions 1203', 1204', 1205', 1206' are then fastened into knots 1231', 1232', 1233', 1234' adjacent pledgets 1221, 1222, 1223, 1224. Another embodiment may include a clip type mechanism (e.g., similar to cinching mechanism 912, 913 of FIG. 9B) securing the prosthetic to tissue, with the same ePTFE suture loops affixed to that clip mechanism.

In an embodiment the independent loops of the prosthetic will serve as artificial chordae tendinae during mitral valve surgery. As they are integrated into the prosthetic and do not require assembly or measurement, they will save the surgeon time.

In an embodiment the suture components of the system of FIG. 12A, FIG. 12B, FIG. 13A, FIG. 13B, and FIG. 13C will be ePTFE monofilament suture, the pledgets will include PTFE felt, and the surgical needles will be 302 Stainless Steel. However, other embodiments are not so limited.

Uses include mitral valve repair surgery and atrioventricular (tricuspid) valve repair surgery (as that valve also has chordae tendinae which could potentially be replaced), but other embodiments are not so limited.

Figure 21:
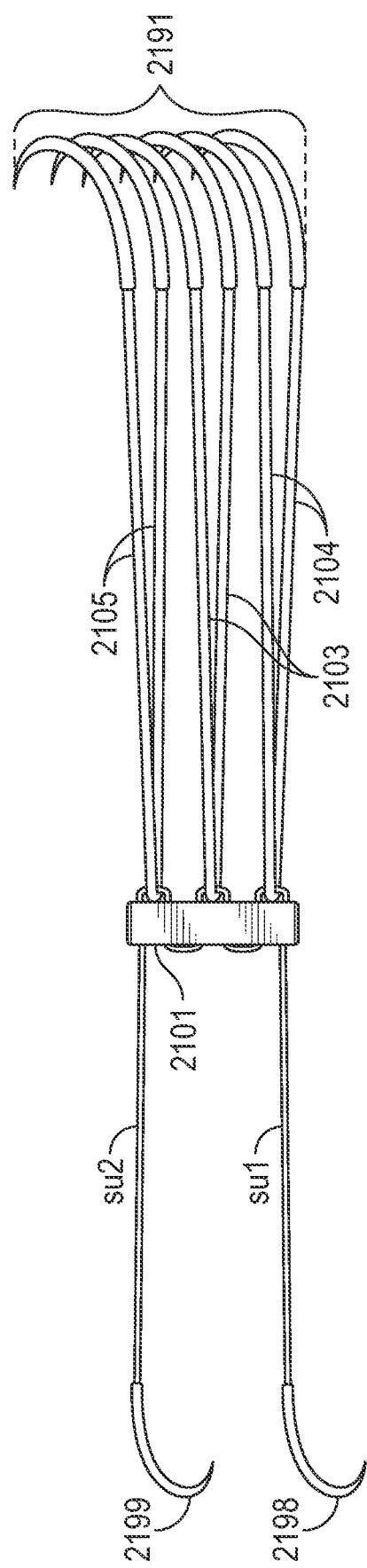

FIG. 21 depicts a chord repair system. Similar to the embodiment of FIG. 12A, suture lengths Su1 and Su2 (which are part of a monolithic or single-piece suture length) couple to needles 2198, 2199 and pledget 2101 (and pledget 2102 after Su1 and Su2 are advanced through papillary tissue in FIG. 22B). Furthermore, length pairs 2105, 2103, 2104 couple to needles 2191. However, notice no knots analogous to knots 1231, 1232, 1233, 1234 (adjustable or fixed) exist in the embodiment of FIG. 21. FIG. 21 has adjustable chord lengths. As shown in FIG. 22A, FIG. 22B, FIG. 22C, suture length pairs 2105, 2103, 2104 pass through leaflet 2190. Valve leaflet 2190 may slide along these pairs, thereby rendering the chord lengths as variable in length. A maximum deployable length is set by creating knots 2121, 2122, 2123 or other coupling mechanisms atop or superior to the leaflet.

Figure 23A:
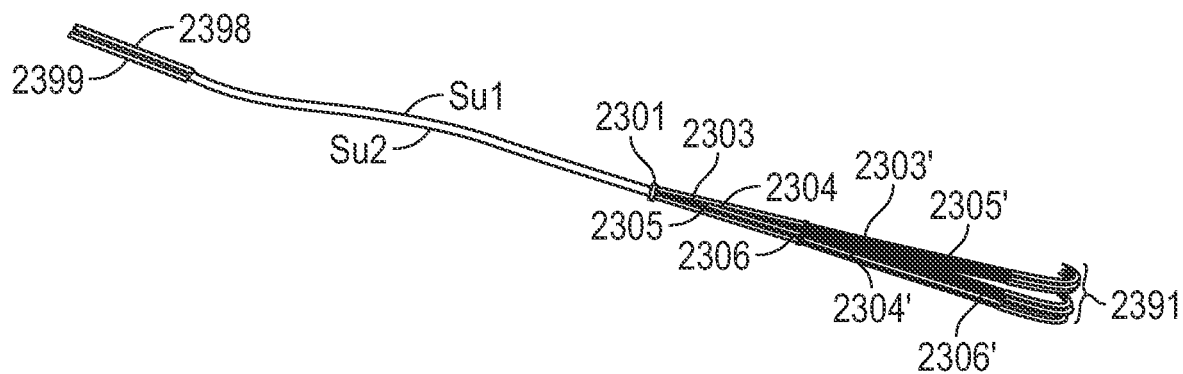
FIGS. 23A, 23B, 24, 25, 26, 27 and 28 depict a method and system for ferrule-based chord replacement.
Figure 23B:
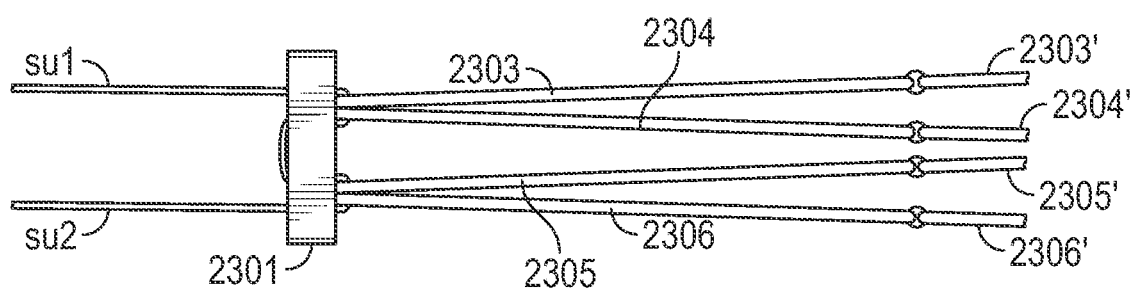

FIG. 23A, FIG. 23B, FIG. 24, FIG. 25, FIG. 26, FIG. 27 and FIG. 28 include a chord repair system. The embodiment of FIG. 23B is similar to that of FIG. 12B. Furthermore, the embodiment of FIG. 23A is similar to that of FIG. 12A. However, in FIG. 23A Su1 and Su2 lengths do not terminate in needles but instead terminate in ferrules 2398, 2399. A ferrule may include a ring or cap or adhesive (or other coupler) attached to a coupling member, such as suture. The ferrule may include an aperture that provides a resistive fit to a needle. Similar to the ferrule shown in FIG. 17A, FIG. 17B, FIG. 17C, FIG. 17D and FIG. 17E, addressed below, in an embodiment a ferrule cinches tightly to a suture at one end of the ferrule. At the other end of the ferrule an aperture exists to receive a needle.

Figure 24:
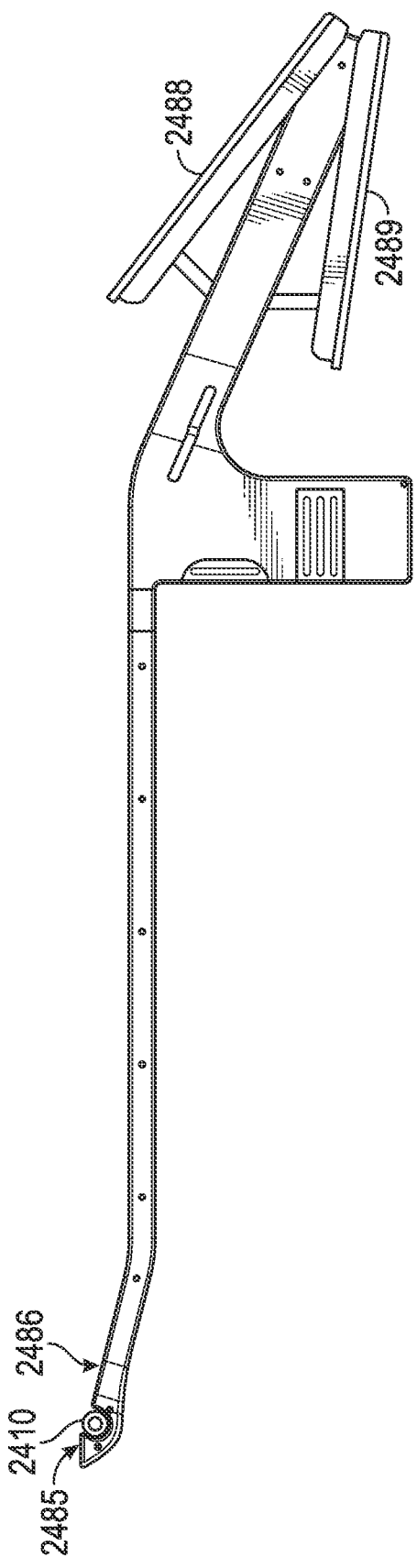
Figure 25:
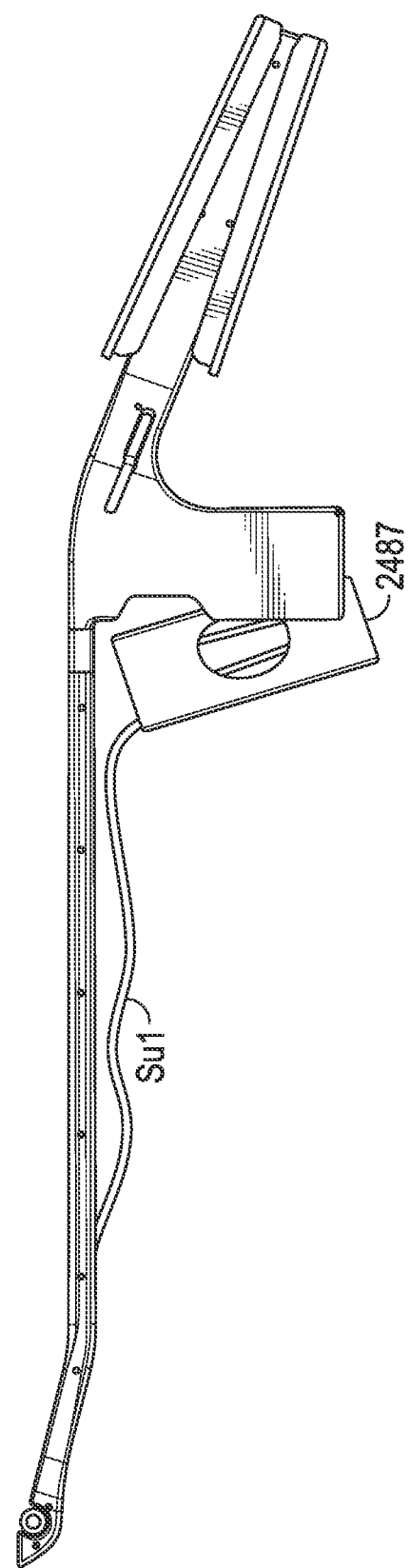

With ferrules 2398, 2399 in mind, attention turns to FIG. 24 wherein a tool includes a distal portion having an aperture to accommodate papillary muscle 2410. Tip 2485 includes ferrules 2398, 2399 (not shown as they are deployed within tip 2485), which connect to Su1, Su2 (not shown but present within the deployment device). At location 2486 two needles are connected to a driving mechanism (e.g., linkage system) such that compression of handles 2488, 2489 drives the needles across papillary tissue 2410 and into ferrules 2398, 2399. The needles are then retracted away from tip 2485, back through tissue 2410, and towards location 2486. As a result the deployment tool has now threaded Su1, Su2 through tissue 2485. After doing so, in FIG. 25 Su1 (and Su2, although not shown) and cartridge 2487 may be removed from the apparatus. Cartridge 2487 may include loop members 2303, 2304, 2305, 2306.

Figure 26:
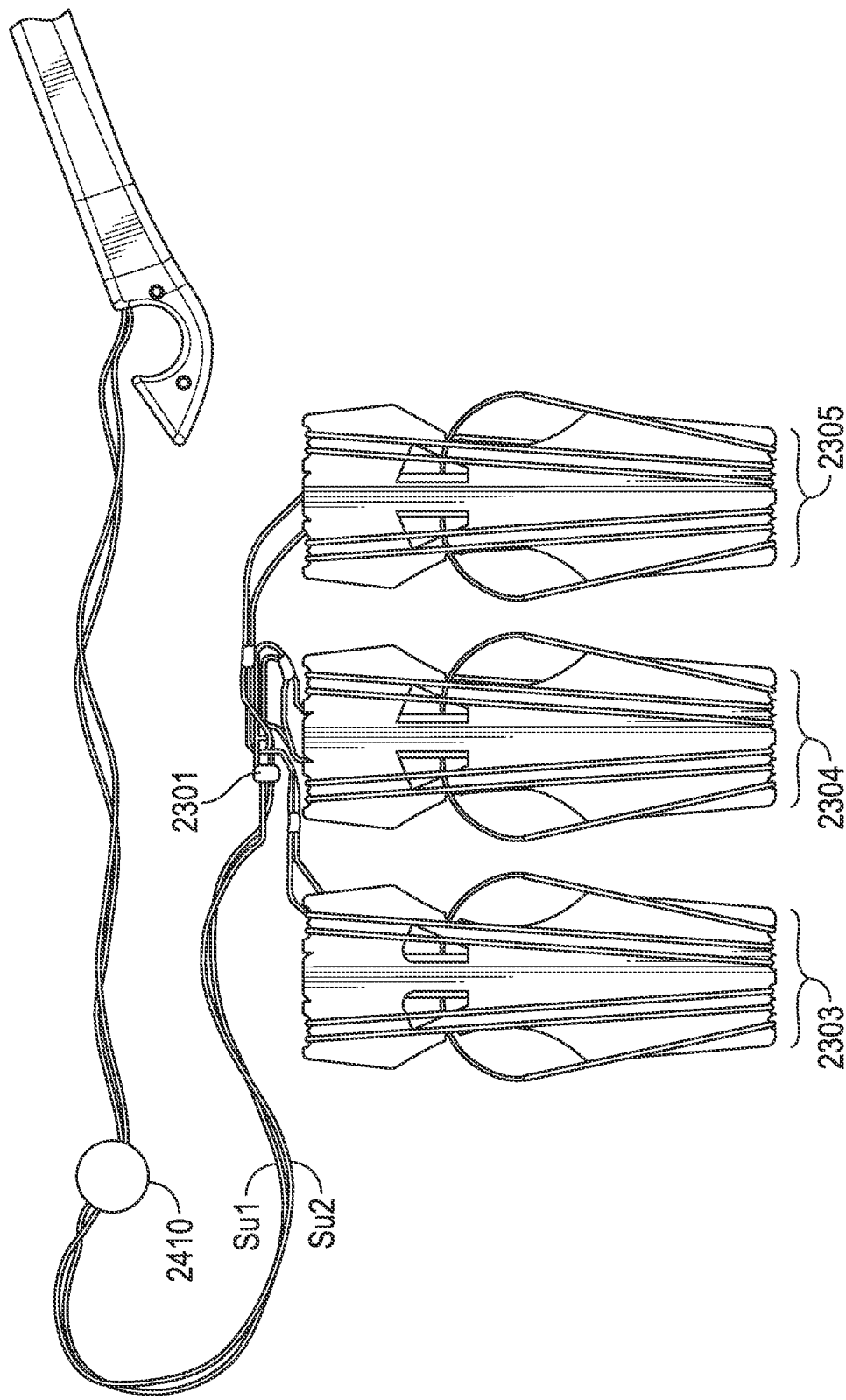
Figure 27:
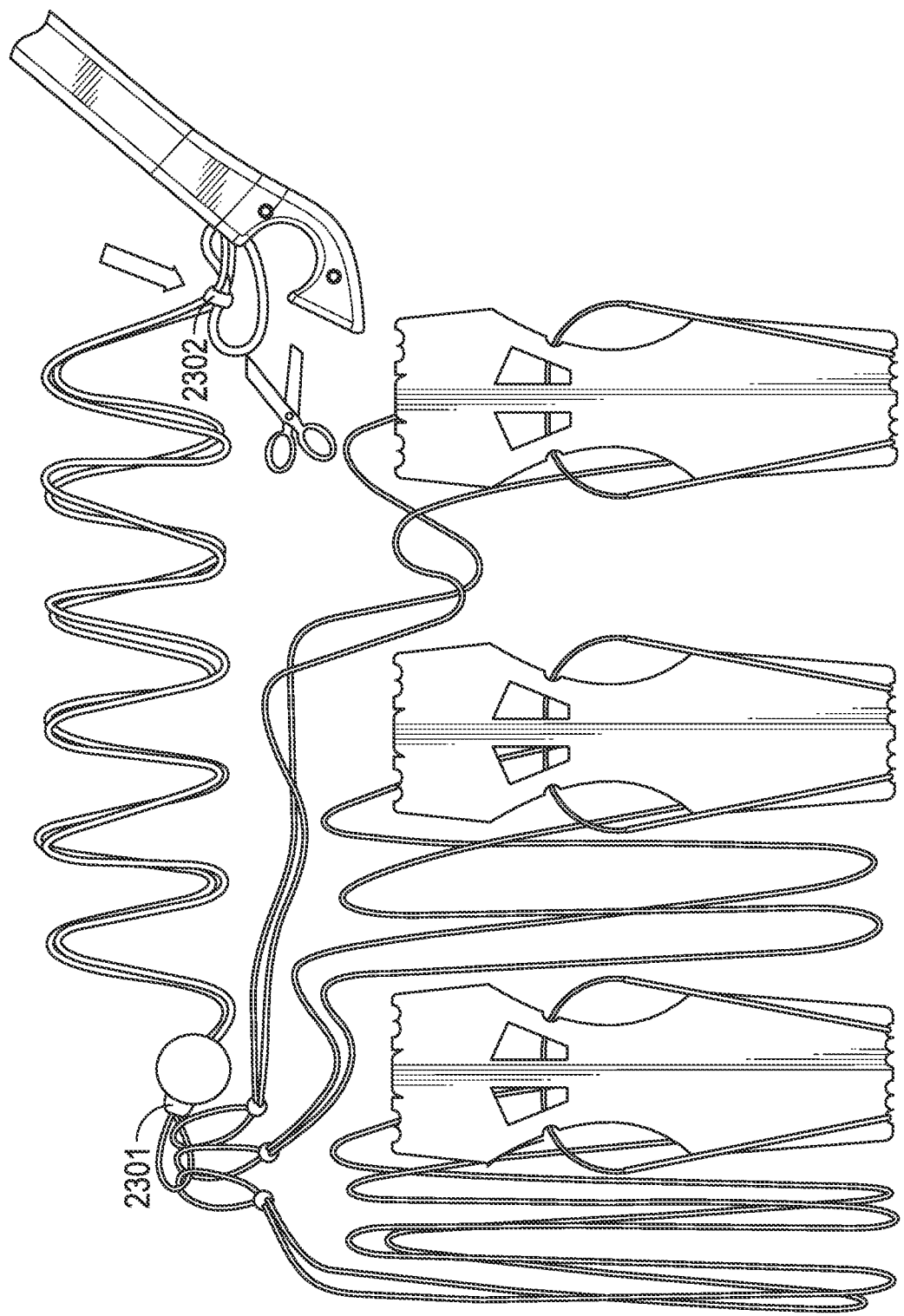
Figure 28:
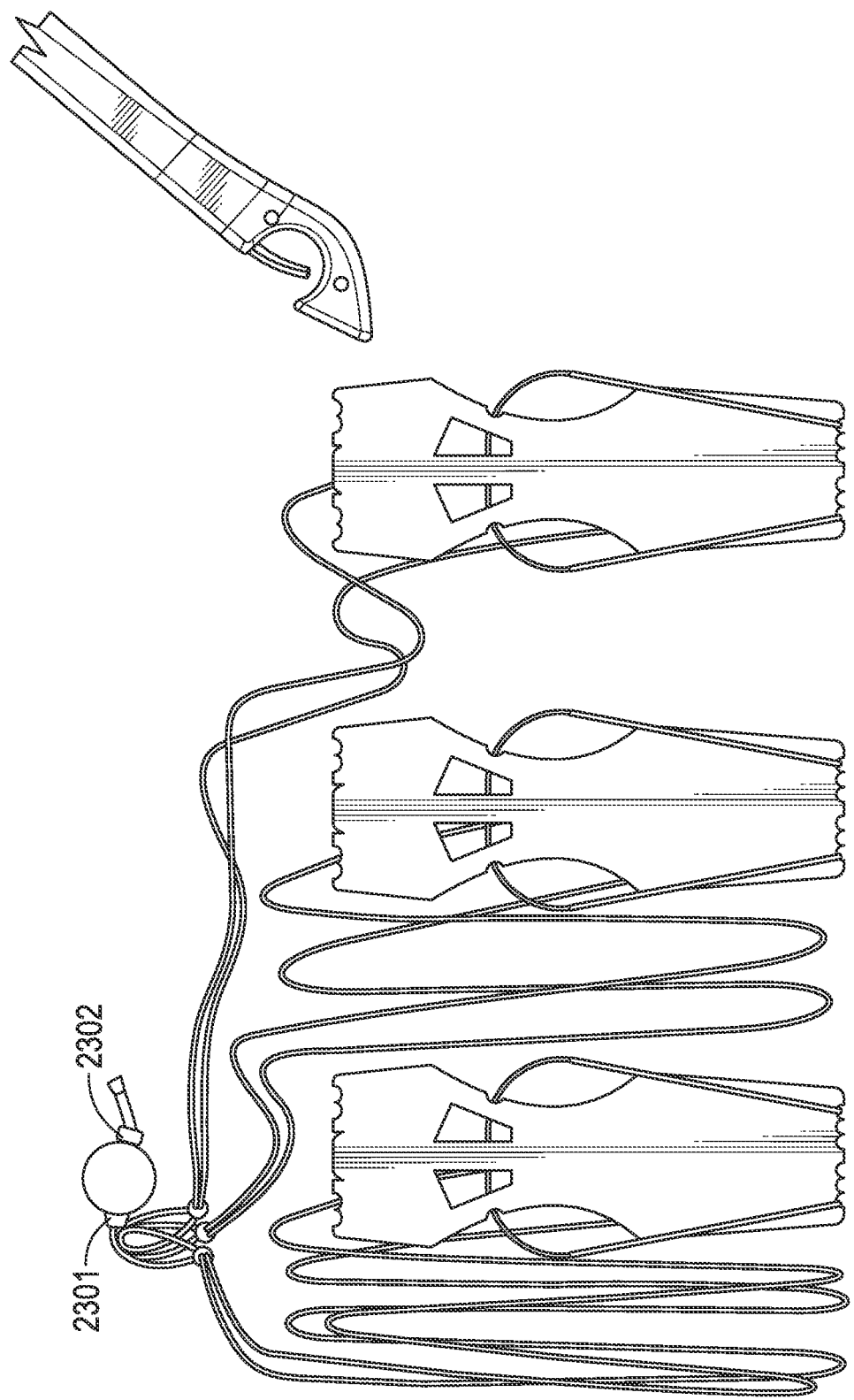

In FIG. 26 ferrules 2398, 2399 are now withdrawn into the tool (and not visible in this figure) and loop members 2303, 2304, 2305 have been removed from cartridge 2487 (and shown wrapped around a basic storage chassis that keeps suture lengths from tangling and for keeping needle tips protected). (Loop member 2306 has been removed in this Figure for ease of illustration. However, loop member 2306 may also have been removed due to surgeon discretion.) Suture portions Su1, Su2 extend through tissue 2410 and couple loop members 2303, 2304, 2305 to tissue 2410. In FIG. 27 the surgeon has slipped pledget 2301 down Su1, Su2 to be proximal to the papillary muscle, has removed pledget 2302 from the device, and is about to cut a tether that keeps pledget 2302 tethered to the tool (however in other embodiments no such tethering exists). In FIG. 28 the tether has been cut and is no longer visible and the surgeon has moved both pledgets 2301, 2302 along Su1, Su2 proximal to the papillary tissue. Lengths Su1, Su2 have been shortened and their ends are fastened to one another, adjacent to pledget 2302, with a series of surgeon applied knots, crimps, adhesive, or other coupling system.

Figure 12A:
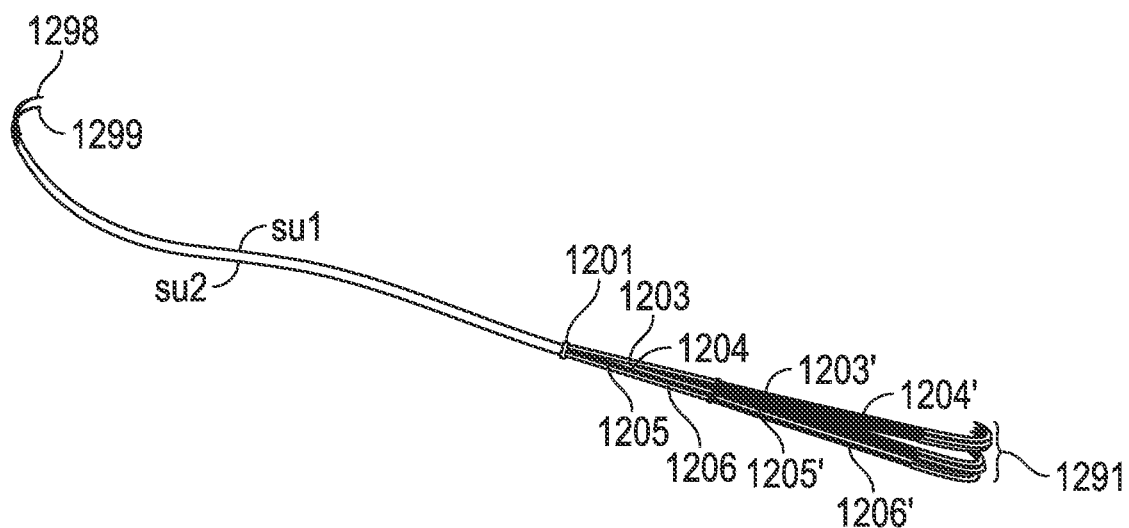
FIGS. 12A, 12B, 13A, 13B, and 13C depict methods and systems for multi-chord replacement in various embodiments of the invention.
Figure 12B:
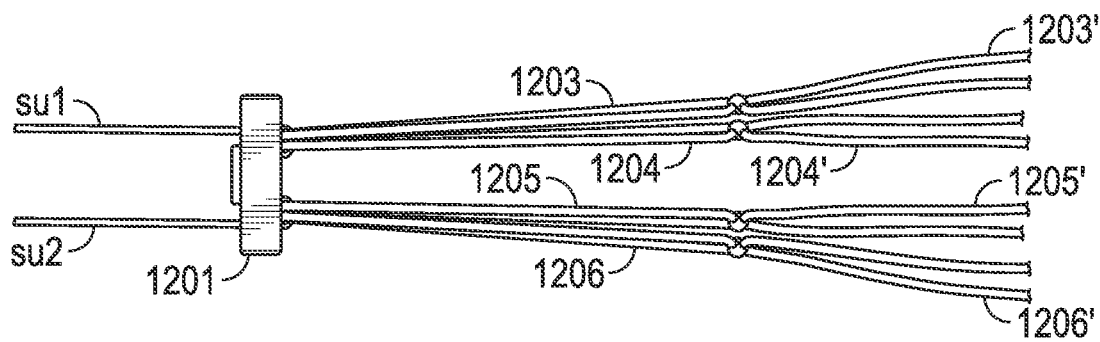

Thus, FIG. 12, FIG. 12B and FIG. 21 show systems that may be implemented by hand (e.g., via keyhole surgery or open-heart surgery) and FIG. 23A, FIG. 23B, FIG. 24, FIG. 25, FIG. 26, FIG. 27 and FIG. 28 show how a deployment apparatus may be used (e.g., during keyhole surgery) to facilitate deployment. While not shown, in another embodiment needles 2391 may be replaced with ferrules so they too (in a manner similar to ferrules 2398, 2399) may be captured with a needle in a deployment tool (like that shown in FIG. 24) and brought through leaflet tissue in a manner analogous to how ferrules 2398, 2399 are brought across papillary tissue. In other words, some or all needles may be replaced with ferrules and vice versa depending on how the system is deployed.

FIG. 14, FIG. 15A, FIG. 15B, FIG. 16A, FIG. 16B and FIG. 16C include knotless chord repair systems. The knotless chord repair systems allow for quick adjustment of repair chord length to accommodate the anatomic specifics of the individual patient. In an embodiment disclosed in FIG. 14 an artificial chordae prosthetic is made from ePTFE suture that results in a permanent implant for chordae tendinae replacement. The embodiment has four independent loops (leaflet loop, fine adjustment loop, gross adjustment loop, papillary loop) that can be cut and removed if the surgeon wants three or less loops (but other embodiments are not so limited regarding the number of loops). This is an advantage since such embodiments can withstand a segment being cut without the whole system unraveling.

Figure 14:
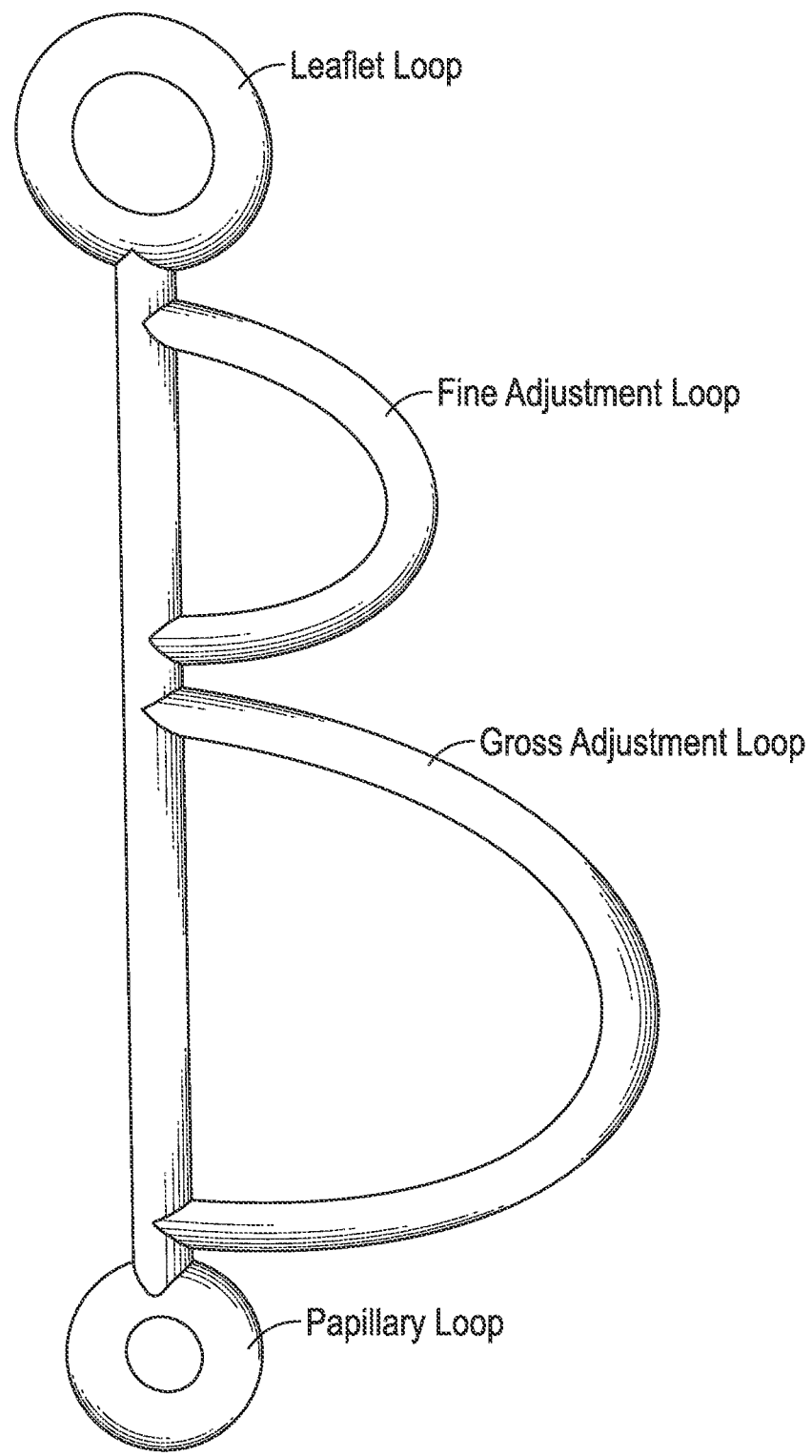
FIGS. 14, 15A, 15B, 16A, 16B, and 16C depict methods and systems for quick and simple knotless multi-chord replacement in various embodiments of the invention.

More specifically, FIG. 14 depicts an embodiment that utilizes compressed and/or sintered PTFE that is formed to configuration. The leaflet loop may be sutured to tissue (e.g., valve leaflet) and the papillary loop may be sutured or otherwise secured (e.g., staple) to tissue (e.g., papillary muscle). The linear portion of the fine adjustment loop may be severed to lengthen the overall length of the system in a manner similar to that shown with FIGS. 1-4. If the overall length need not be adjusted then the arc portions of the fine and gross adjustment loops may be removed (or left in place).

Figure 15A:
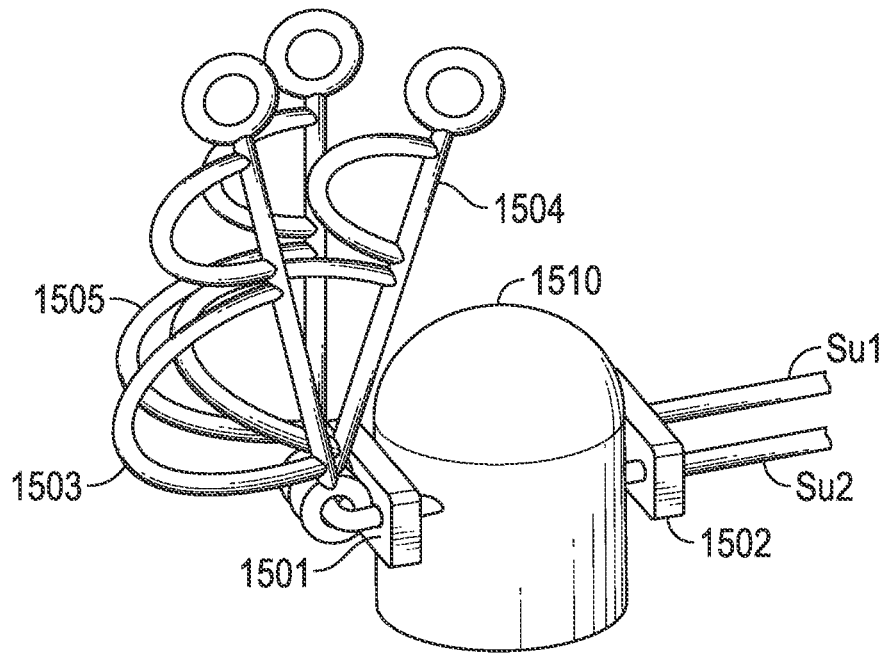
Figure 15B:
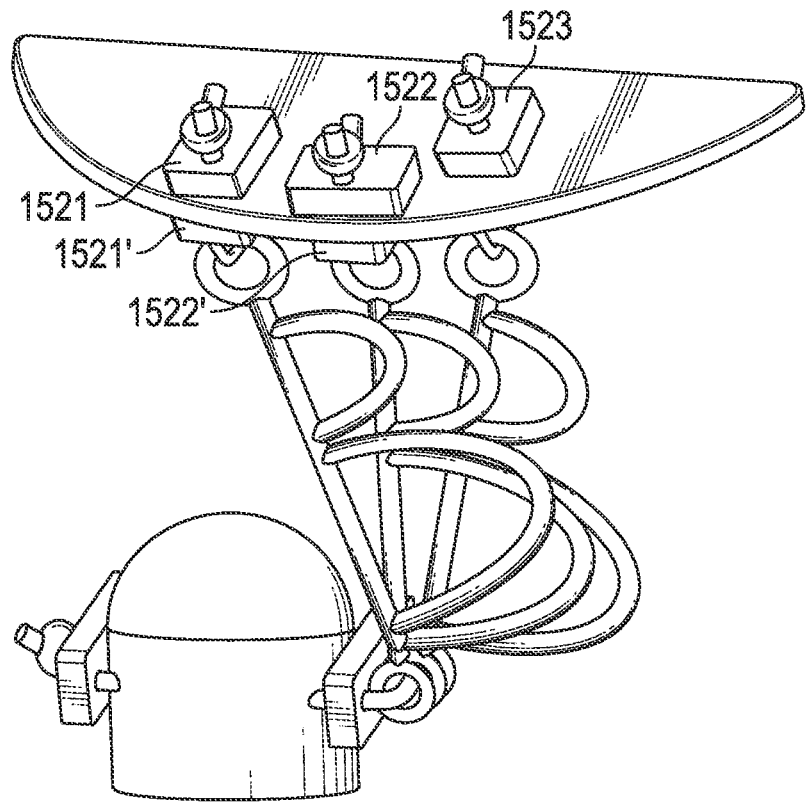

FIG. 15A shows a system similar to the embodiments of FIG. 12A, FIG. 12B, FIG. 13A, FIG. 13B, and FIG. 13C. Three loop members 1503, 1504, 1505 couple to suture having suture lengths Su1 and Su2. The suture passes through pledgets 1501, 1502 and tissue 1510 (e.g., cardiac wall such as ventricular wall). Su1 and Su2 may tie off one another adjacent pledget 1502. FIG. 15B shows leaflet loops sutured to pledgets 1521, 1522, 1523 on top/superior surface of a leaflet and pledgets 1521', 1522' (and a third pledget not shown as it is obscured by the leaflet) on the bottom/inferior surface of the leaflet, along with surgeon tied leaflet knots. In an embodiment, the leaflet loop adjacent the leaflet may couple to suture lengths analogous to lengths 1203' of FIG. 12A where the two lengths (which are included within a monolithic suture segment) each couple to a needle that can be advanced through the leaflet and then tied off to form the knot on the pledget on the superior surface of the leaflet.

Figure 16A:
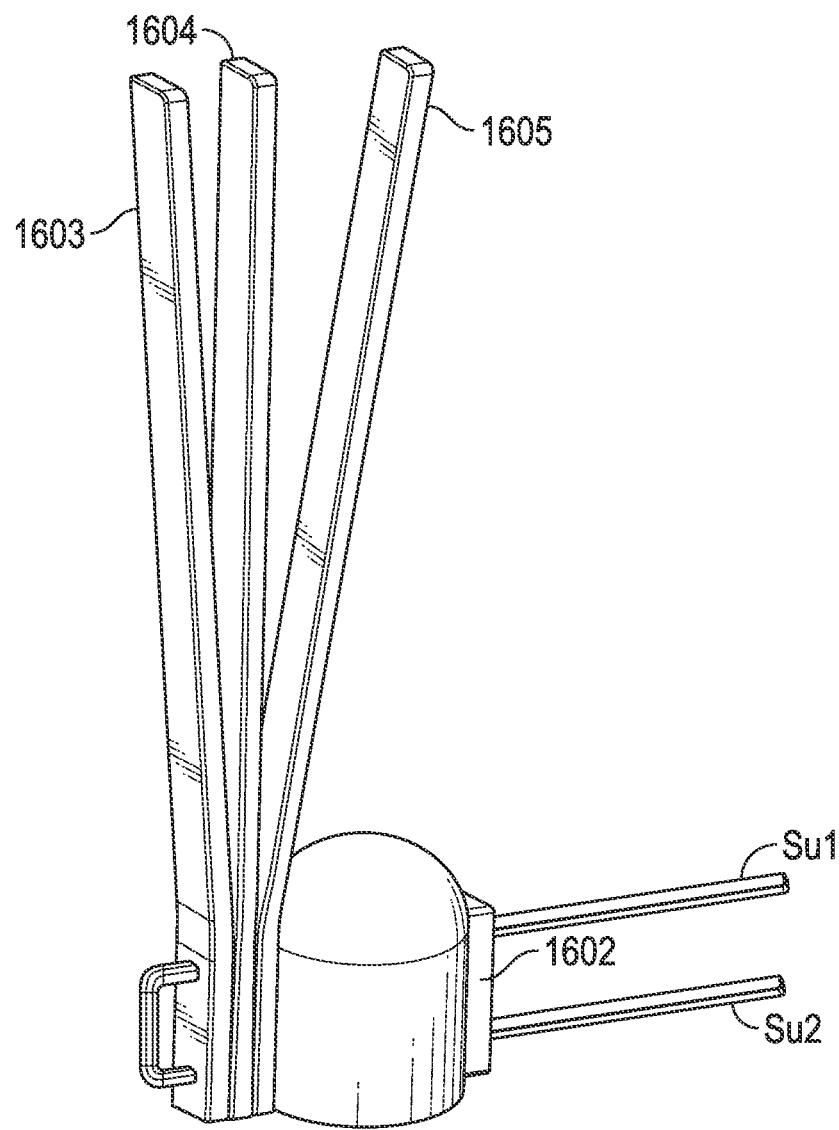
Figure 16B:
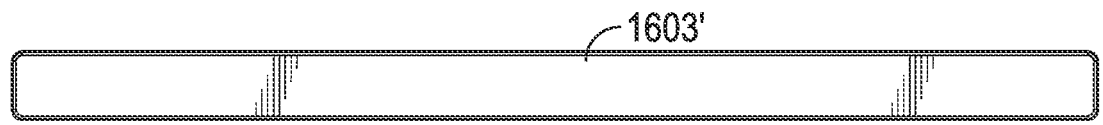
Figure 16C:
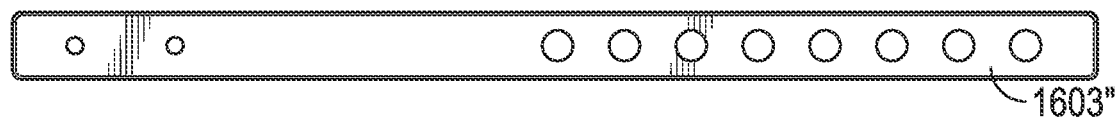
Figure 17A:
FIGS. 17A, 17B, 17C, 17D, 17E depict a method and system for ferrule to suture coupling in an embodiment of the invention.
Figure 17B:
Figure 17C:
Figure 17D:
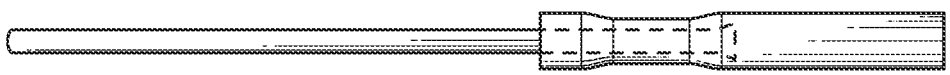
Figure 17E:

FIG. 16A is similar to that of FIG. 15A but shows strips 1603, 1604, 1605 (and not loops) coupled to pledget 1602 with suture portions Su1 and Su2. Strips 1603, 1604, 1605 may be solid (e.g., see member 1603' of FIG. 16B) and made of felt (e.g., PTFE felt) or may have apertures (e.g., see member 1603" of FIG. 16C).

A first example of the "knotless looped ladder" includes a system comprising: a first loop including first and second segments that directly connect to each other and fully form the first loop; and a second loop including third and fourth segments that directly connect to each other and fully form the second loop; wherein (a) the first and second loops are monolithic with one another and include no knots, and (b) the first and second segments have unequal lengths, and the third and fourth segments have unequal lengths. In an embodiment one or both of the loops may be non-circular loop. A non-circular loop may include a "D" shaped loop or other such configuration but does not include a perfectly circular loop. However, other embodiments include circular loops.

A second example of the "knotless looped ladder" system includes the subject matter of the first example of the "knotless looped ladder" system wherein none of the first, second, third, and fourth segments have equal lengths.

A third example of the "knotless looped ladder" system includes the subject matter of the first example of the "knotless looped ladder" system wherein a fifth segment includes an end that directly connects to the first loop at a junction between the first and second segments that directly contact one another; wherein the fifth segment includes another end that does not directly contact the first loop. In an embodiment the fifth segment may couple to a needle. In an embodiment the fifth segment may couple to a ferrule.

A fourth example of the "knotless looped ladder" system includes the subject matter of the 1-3 examples of the "knotless looped ladder" system wherein the fifth segment is monolithic with the first and second loops.

A fifth example of the "knotless looped ladder" system includes the subject matter of the first "knotless looped ladder" example comprising: a third loop including sixth and seventh segments that directly connect to each other and fully form the third loop; and a fourth loop including eighth and ninth segments that directly connect to each other and fully form the fourth loop; wherein (a) the third and fourth loops are monolithic with one another, include no knots, and are not monolithic with the first and second loops, and (b) the fifth and sixth segments have unequal lengths.

A sixth example of the "knotless looped ladder" system includes the subject matter of the fifth "knotless looped ladder" example comprising a pledget coupled to the first, second, third, and fourth loops.

A seventh example of the "knotless looped ladder" system includes the subject matter of the first "knotless looped ladder" example wherein the first and second loops are sintered together.

An eighth example of the "knotless looped ladder" system includes the subject matter of the first "knotless looped ladder" example wherein the system is configured so severing one of the first, second, third, and fourth segments does not generally weaken the structural integrity of the remaining segments.

A ninth example of the "knotless looped ladder" system includes the subject matter of the first "knotless looped ladder" example wherein the system is configured so severing the first segment results in the system having a first overall length and severing the second segment results in the system having a second overall length unequal to the first overall length.

In an embodiment the first and second segments may include separate ePTFE strands joined together via heat (e.g., laser), weld, chemical reaction, and the like.

FIG. 17A, FIG. 17B, FIG. 17C, FIG. 17D and FIG. 17E depicts a system and method for coupling chord/suture to a ferrule. This system may be used, for example, to receive a needle within the ferrule. In one embodiment, a needle is forced through papillary muscle, as described above, mated with a ferrule (that is attached to suture), and withdrawn back through the muscle pulling the suture through the muscle. The suture may then be fastened adjacent a pledget.

However, other embodiments are not so limited. Other embodiments generally concern coupling a ferrule to chord or suture. The chord or suture may include materials discussed elsewhere herein. Embodiments improve over conventional systems where ePTFE suture is crimped into a blind hole in the end of a needle. For example, an embodiment where an enlarged "flare" at the end of the suture is pulled back against a crimped section of the tube is an improvement over conventional systems where crimping onto the ePTFE alone can cause cutting of the ePTFE that reduces the pull-put force significantly. By forming a "flare" on the end of the suture, it is not necessary to crimp as much onto the ePTFE suture. This reduces the likelihood of cutting the material as well as provides a much stronger pull-out force than a crimp alone.

More specifically, in FIG. 17A, FIG. 17B, FIG. 17C, FIG. 17D and FIG. 17E an embodiment swages a needle to suture. In step 1 suture is threaded through a ferrule. In step 2 suture, such as ePTFE suture, is heated to expand or flare. In step 3 the ferrule is crimped to the same diameter as the suture. In step 4 the suture is retracted to force the flared portion of suture against the crimped portion of the ferrule. Finally, in step 5 the ferrule is crimped still further to secure the suture within the ferrule. The ferrule may be coupled (monolithically or non-monolithically) to a needle. Other embodiments may omit certain steps. For example, the a single crimping may occur instead of the two crimping steps described above. This single crimping may occur before or after the suture is flared. The single crimping may be to the original thread diameter or to a smaller diameter.

FIG. 18A, FIG. 18B, FIG. 18C, FIG. 18D, FIG. 18E, FIG. 18F, FIG. 18G, FIG. 19A, FIG. 19B, FIG. 19C, FIG. 19D, FIG. FIG. 19E, FIG. 20A, FIG. 20B, FIG. 20C and FIG. 20D concern an embodiment that includes a fully or partially pre-constructed prosthetic to be used during heart surgery (e.g., open heart surgery, percutaneous valve repair) for valve repair (e.g., mitral valve repair). Such an embodiment eliminates/reduces the knots associated with conventional artificial chordae prosthetics. In some embodiments all knots are eliminated, whether the knots are pre-fabricated by a medical device vendor or fabricated during surgery by the medical team. In other embodiments, the number of knots is at least reduced.

The embodiments of FIG. 18A, FIG. 18B, FIG. 18C, FIG. 18D, FIG. 18E, FIG. 18F, FIG. 18G, FIG. 19A, FIG. 19B, FIG. 19C, FIG. 19D, FIG. 19E, FIG. 20A, FIG. 20B, FIG. 20C and FIG. 20D improve device strength over current methods. Tying knots de-rates/lowers the strength of the base material (e.g., suture). The knots introduce stress concentrations, which cause the knot to fail at a smaller load than the base material. Thus, eliminating/reducing the knots will improve the failure strength of the base material.

The embodiments of FIG. 18A, FIG. 18B, FIG. 18C, FIG. 18D, FIG. 18E, FIG. 18F, FIG. 18G, FIG. 19A, FIG. 19B, FIG. 19C, FIG. 19D, FIG. 19E, FIG. 20A, FIG. 20B, FIG. 20C and FIG. 20D reduce variability over current methods. A current method of hand tying artificial chordae prosthetics out of ePTFE suture requires skill on the part of the surgeon. Each knot is comprised of between eight to ten throws in ePTFE suture. The knots could be tied incorrectly or the surgeon could miscount the requisite number of throws resulting in an inferior knot. By eliminating the knots altogether, an embodiment eliminates the variability that can be observed in the current method of hand tying artificial chordae prosthetics.

An embodiment reduces operating room (OR) time compared to current methods. Since the prosthetic is not fabricated during surgery, the duration that the patient is on cardiac bypass in the OR is reduced.

An embodiment uses ePTFE suture, but other embodiments are not so limited.

Figure 18A:
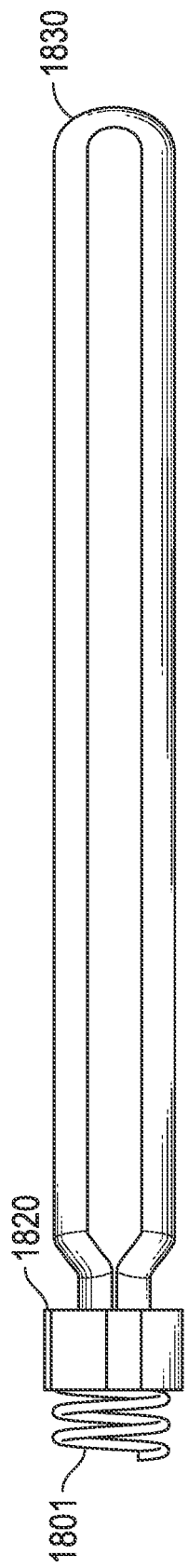
FIGS. 18A, 18B, 18C, 18D, 18E, 18F, 18G, 19A, 19B, 19C, 19D, 19E, 20A, 20B, 20C, and 20D depict methods and systems for knotless adjustable chord length replacement in various embodiments of the invention.

As seen in FIG. 18A, "Hub" 1820 may include PEEK but may include other materials (e.g., injection moldable implantable materials) in other embodiments. "Coil" 1801 includes Nitinol in one embodiment, but may be stainless steel or another implantable material (e.g., shape memory alloys) in other embodiments. Loop 1830 may be ePTFE but other materials are also possible.

An embodiment is for artificial chordae repair of the mitral leaflet during open heart surgery on a stopped heart but other embodiments are not so limited and may be used for, as an example, percutaneous chordal repair, and/or other suture based medical procedures (generally fixing two portions of tissue to one another).

While conventional methods require knots to be tied during surgery, either to anchor the prosthetic to the papillary muscle or to the mitral valve leaflet, an embodiment requires no knots at any time.

Figure 18B:
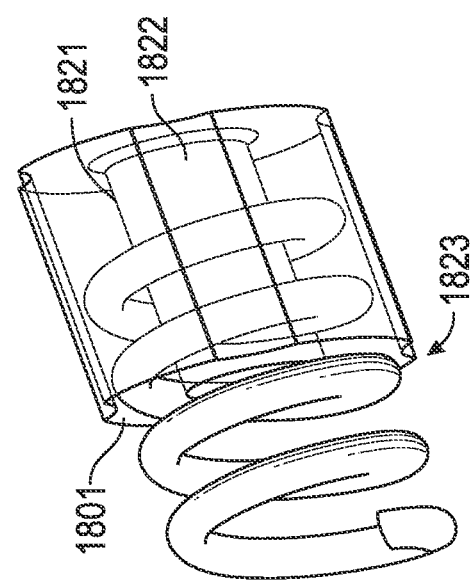

FIG. 18B includes a "shoulder" 1821 for the inner passage way 1822 of hub 1801. In an embodiment the inner passage has a consistent inner diameter (ID) running from its proximal end to its distal end (which will be closed to the papillary muscle when implanted). However, in another embodiment (FIG. 18B) the inner passage flares out near the distal end 1823 so that the inner diameter gradually decreases as the passage goes from its distal end towards its midpoint.

Figure 18C:
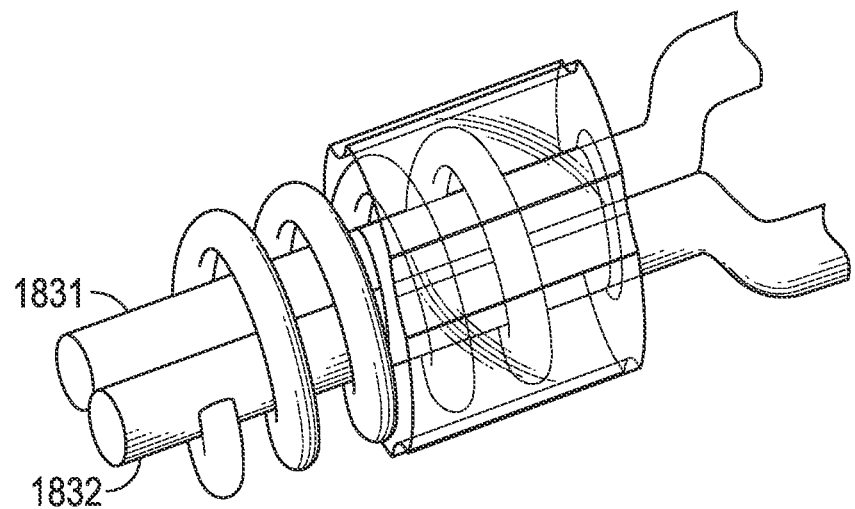
Figure 18D:
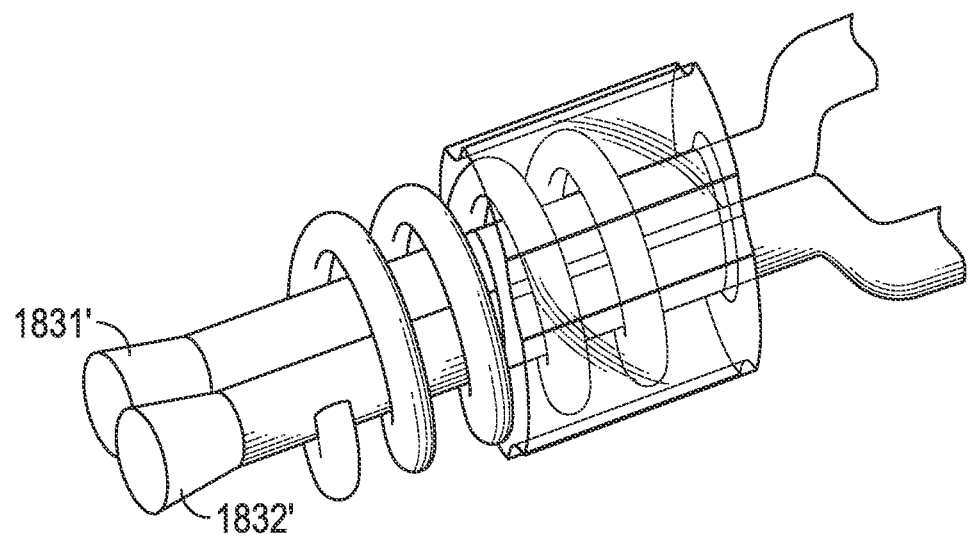
Figure 18E:
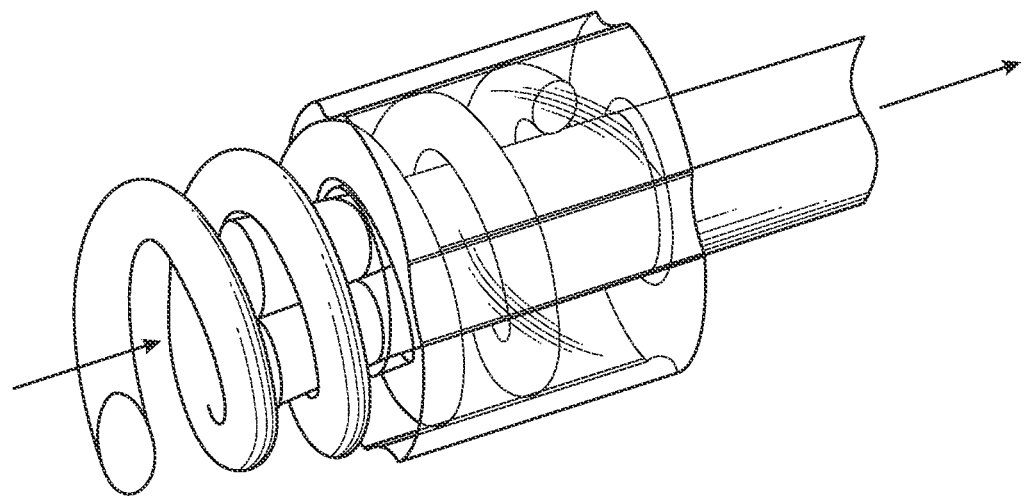
Figure 19A:
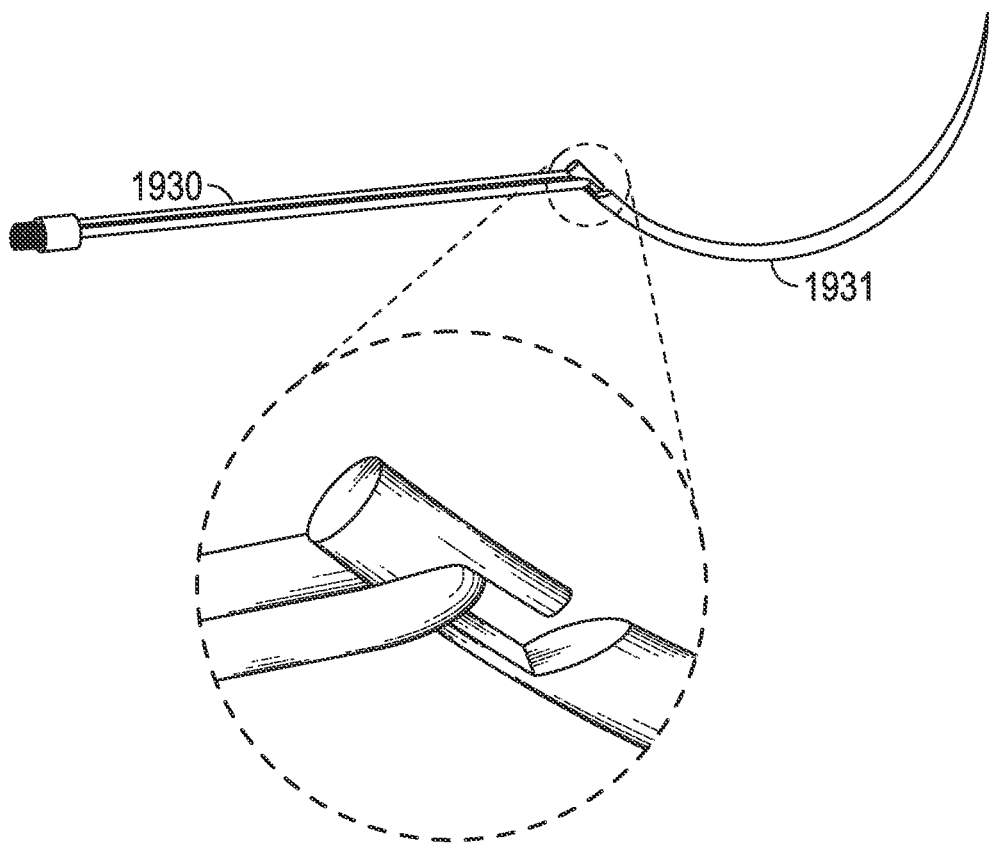
Figure 19B:
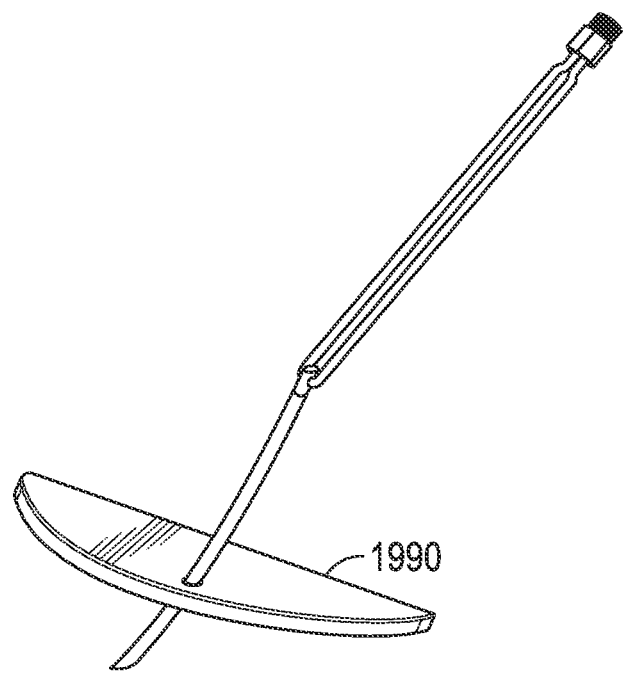
Figure 19C:
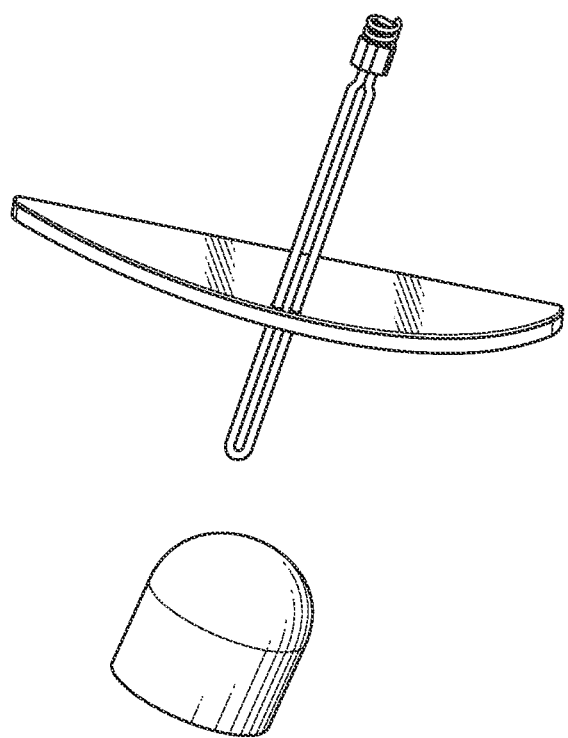
Figure 19D:
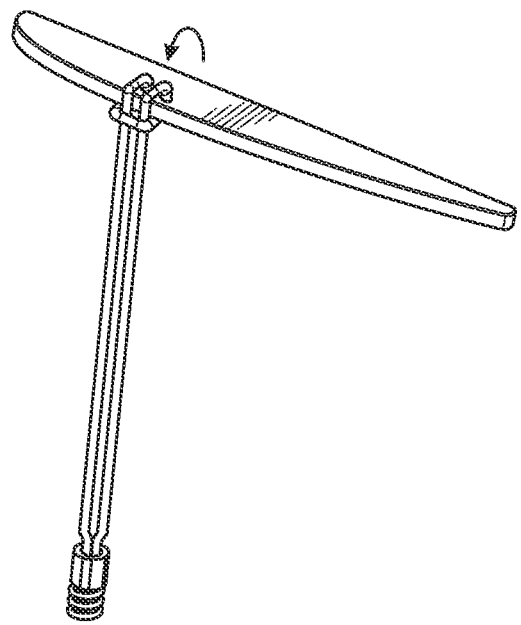
Figure 19E:
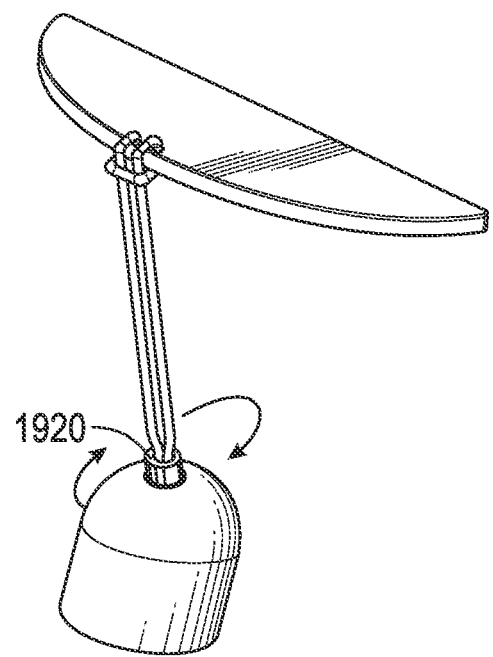
Figure 20A:
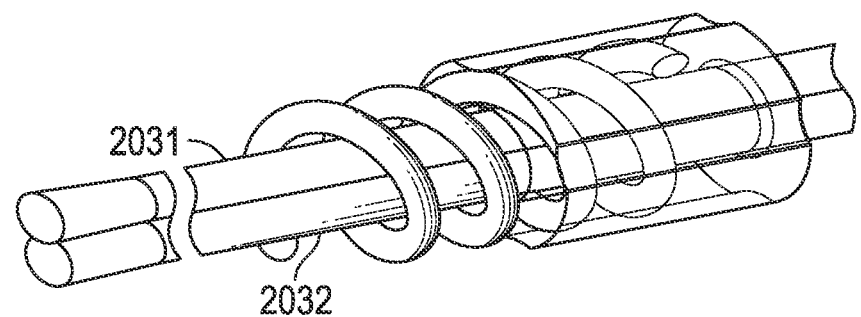
Figure 20B:
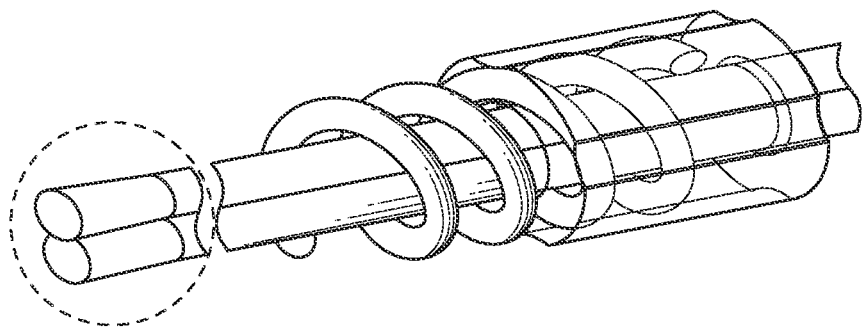
Figure 20C:
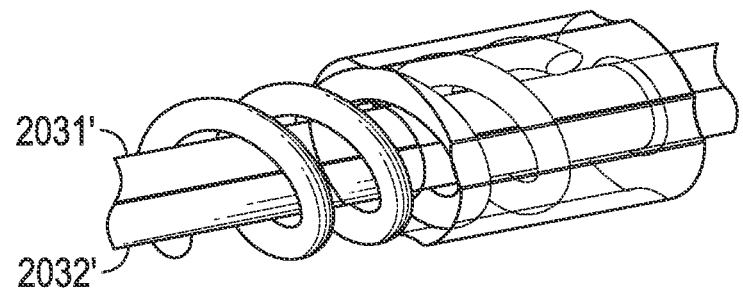
Figure 20D:
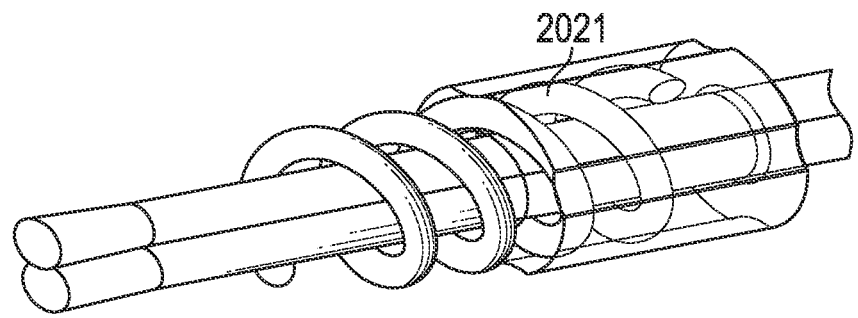

FIG. 18C shows suture length portions 1831, 1832 of suture 1830. Suture length portions 1831, 1832 pass through hub 1820 and then (FIG. 18D) the ends (which may be ePTFE in an embodiment) 1831', 1832' are heated to flare out. As seen in 18D-G those ends are then pulled partially through hub 1801 to wedge against shoulder' 1821. Then, in FIG. 19A loop 1930 is coupled to needle 1931, advanced through leaflet 1990 (FIG. 19B and FIG. 19C), looped upon itself (FIG. 19D), and finally hub 1920 and the coil are secured to tissue (e.g., papillary muscle) as shown in FIG. 19E by screwing the coil into the tissue.

Figure 18F:
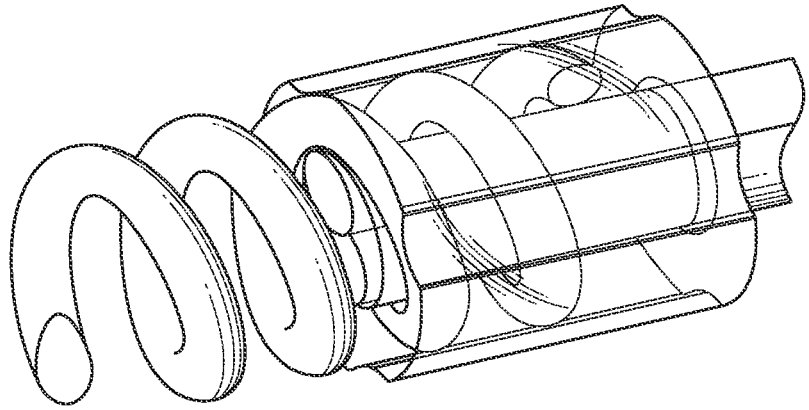
Figure 18G:
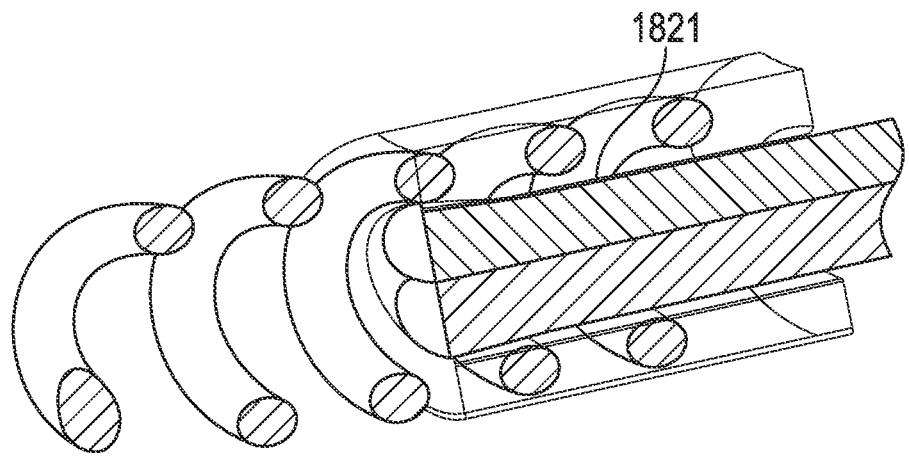

FIGS. 20A-D show a method for chord length adjustment whereby, upon a surgeon determining the chord length is too long, the surgeon cuts suture lengths 2031, 2032 (see FIG. 20A and FIG. 20B), heats ends 2031', 2032' (FIG. 20C and FIG. 20D) and again seats those ends against shoulder 2021 as was shown in FIG. 18F.

In another embodiment the hub may be separably coupled to the corkscrew member. For example, to couple the hub to the corkscrew member the hub may be advanced along the corkscrew by moving the hub from the proximal end of the coil towards the distal end of the coil (which is closest to the papillary muscle upon implantation) by rotating the hub clockwise (i.e., screwing the hub onto the coil). This is reversible in one embodiment. Thus, to change the chord length the user can simply unscrew the hub from the coil member (rotate hub counterclockwise) and then trim one or both of the chord lengths, reheat the newly trimmed length(s), and then screw the hub back onto the coil member with the newly shortened chord length(s) in tow.

In an embodiment the user may vary the length of coupling between the hub and coil member. In an embodiment the user may adjust how far distally he or she advances the hub over the screw/coil to vary the length of the chord (i.e., the distance between the valve leaflet and the papillary muscle). In an embodiment a lock washer may be located between the hub and the proximal end of the chords (i.e., the valve leaflet). After the user finishes adjusting chord length the lock washer or lock nut may be advanced to couple to the hub and/or corkscrew member to thereby prevent the hub from unscrewing from the corkscrew member post implantation. Thus, while FIG. 18A, FIG. 18B, FIG. 18C, FIG. 18D, FIG. 18E, FIG. 18F, FIG. 18G, FIG. 19A, FIG. 19B, FIG. 19C, FIG. 19D, FIG. 19E, FIG. 20A, FIG. 20B, FIG. 20C and FIG. 20D illustrate the corkscrew proximal end always firmly enclosed within the hub in other embodiments that is not necessarily the case. Thus, the lock nut could advance over a portion of the coil before snugly mating against the proximal portion of the hub. The lock nut distal end and the hub proximal end may have reciprocating edges (e.g., teeth) that couple to resist rotation. In an embodiment an intermediate washer having reciprocating teeth may couple between the lock nut and hub (which also have teeth on their facing edges) to lock in with the intermediate washer (which may be sized to freely rotated about the coil to allow it to freely adjust and couple the lock nut and the hub).

In an embodiment a staple or cinch may be coupled to the distal chord ends. Thus, instead of (or in addition to) heating the chord ends a cinch/staple/crimped metal sleeve may be attached to the distal chord ends. The cinch (a.k.a., termination member) may be sized to fit within the corkscrew member but not advance fully through the inner passage way of the hub.

In an embodiment the hub may include a slit in its sidewall. That slit may allow the user to pull the chord length(s) into the slit. The slit may have a gradually decreasing width so the chords may "jam", cinch, or wedge into the small width portion of the slit. This may allow the user to reversibly vary the length of the chords for ideal chord length. An outer sleeve may be located at the distal end of the hub upon implantation. The slit may be located in the hub near the midpoint and/or proximal region of the hub. After adjusting chord length in the slit the outer sleeve may be advanced proximally to advance over the slit thereby putting presser on the chord(s) to ensure the chord(s) stay cinched. The outer sleeve may function as a lock nut to lock into place over the hub.

In an embodiment the hub may have a single loop (e.g., coupled to the hub proximal end) to which the chords are knotted. Thus, some embodiments do not exclude all knots but merely lessen the number of knots needed (or how the knots are implemented such as against a hub instead of against tissue, wherein the hub is unlikely to shrink, swell, tear, and the like).

An embodiment includes a system comprising a coil, a hub configured to couple to the coil, and a loop coupled to the hub. In and embodiment the loop includes two ends having greater diameters than an inner portion of the loop. In an embodiment the hub includes an inner channel have a narrowing inner diameter. In an embodiment the most narrow portion of the narrowing inner diameter is smaller than the combined diameters of the two ends of the loop.

Various embodiments are discussed above. Again, conventional methods involve hand tying of an inferior prosthetic (loops are not removable) during surgery. However, various embodiments are superior to conventional systems (e.g., a system of loops coupled to a pledget) because, for example, loops are removable (e.g., surgeon may clip one or two or three loops from the original four as desired, with no adverse effects to the remaining loops) and with conventional systems one cannot remove one of the loops or the entire product unravels. Other embodiments provide advantages because they have leaflet suture strands and needles integrated and conventional systems have additional components, assembly, and time, in order to fashion a complete prosthetic.

Thus, various embodiments are described above. Additional examples are included below.

A first example includes an embodiment includes a chordal replacement system comprising: a pledget coupled to a first chord length and at least one of a first needle and a first ferrule; a second chord length coupled to the pledget and at least a second needle; and a third chord length coupled to the pledget and at least a third needle; wherein the second and third chord lengths are not monolithic with each other and do not constitute a single chord. The pledget may be formed from any of various materials such as, for example, ePTFT, PTFE, PTFE felt, a sheet of PTFE. A pledget is to be interpreted as a buttress or shield to prevent, for example, a suture/coupling member from cutting tissue over time due to repetitive movement of the suture/coupling member. Some embodiments include no pledget. Some embodiments allow for a system to be shipped with no pledget but coupled to a pledget at a later time once the shipping container is opened and is ready for use by the surgeon. In an embodiment the first chord length couples to a first needle and not any ferrule. In an embodiment the first chord length couples to a first ferrule and not any first needle.

A second example includes the subject matter of example 1 wherein the second and third chord lengths directly connect to the first chord length. For instance, the first chord length may cinch the second and third chord lengths directly against the pledget. There may be no materials between the second and first chord lengths as illustrated in, for instance, FIG. 12B. In FIG. 12B the suture comprising Su1 and Su2 directly contacts each of lengths 1203, 1204, 1205, 1206 but in other embodiments the suture comprising Su1 and Su2 directly contacts any one or more of lengths 1203, 1204, 1205, 1206. Indirect contact may be made through a pledget, spacer member (e.g., stainless steel spacer), and the like. In some embodiments the second and third chord lengths may directly contact the pledget but that may not be the case in other embodiments.

A third example includes the subject matter of any or all of examples 1-2, wherein the second chord length couples to a fourth needle and the third chord length couples to a fifth needle. The coupling may direct wherein the chord directly contacts a needle or indirect wherein a chord connects to the needle via a cinch or other coupling member.

A fourth example includes the subject matter of any or all of examples 1-3, wherein the first chord length couples to a sixth needle. For instance, the first chord length may have needles on both of its ends and one of those needles may pass through the pledget, contact the second and third cord lengths (e.g., cinch those chord lengths towards the pledget, be configured such that the surgeon can cinch those chord lengths towards the pledget, pass through loops if the chord lengths are fashioned as loops, and the like), and then pass through the pledget once again.

A fifth example includes the subject matter of any or all of examples 1-4, wherein the second chord length includes a loop that is formed without any knots.

A sixth example includes the subject matter of any or all of examples 1-5, wherein the loop is monolithic and directly connects to no joint. For instance, a loop may be formed without knots via sintering, molding, machining processes and the like. Such a loop may have no knots that hold it together. Such a loop may have improved strength with no stress focal points that may be associated with knots. Such a loop may have ease of manufacturability over knotted embodiments. A loop may be formed of two lengths that are connected albeit without knots. For example, the two lengths may include ePTFE and the two lengths may be heated and then joined. The heat may be supplied by laser or other heat source.

A seventh example includes the subject matter of any or all of examples 1-6, wherein the second chord length includes at least one of suture, polytetrafluoroethylene (PTFE), expanded polytetrafluoroethylene (ePTFE), nylon, polypropylene, cotton, perlon, polyester, polyglecaprone, polyglecaprone 25, Polyglactin, Polyglactin 910, polyglycolic acid (PGA), polylactic acid, and silk. Thus, not all embodiments necessarily include suture. Other embodiments may include a mesh strip or other such strip such as the strip of FIG. 16B or FIG. 16C.

An eighth example includes the subject matter of any or all of examples 1-7, wherein the second chord length is at least one of molded, extruded, and sintered. For example, the looped embodiment of FIG. 14 may be formed via sintering (e.g., create loop or length by heating powder into a desired form defined by a mold), molding, and the like.

A ninth example includes the subject matter of any or all of examples 1-8, wherein the second chord length includes a loop having at least two joints that couple to one another via first and second segments that are unequal in length to each other. The joints may be two lengths fused together via heating, chemical reaction, and the like.

A tenth example includes the subject matter of any or all of examples 1-9, wherein the at least two joints include at least two knots.

An eleventh example includes the subject matter of any or all of examples 1-10, wherein (a) the first chord length is configured to pass through papillary muscle to couple the pledget to the papillary muscle, and (b) the second and third chord lengths are configured to pass through valve tissue to couple the second and third chord lengths to the valve tissue and provide chordal support between the papillary muscle and the valve tissue.

A twelfth example includes the subject matter of any or all of examples 1-11, wherein the system is knotless. For example, the system of FIG. 21 is knotless as is the system of FIG. 14. Those systems may later be formed into knots or coupled to knots at a later time.

A thirteenth example includes a chordal replacement system comprising: a first pledget coupled to a first suture length and at least one of a first needle and a first ferrule; a first suture loop coupled to the pledget, a first knot, and second and third needles; and a second suture loop coupled to the pledget, a second knot, and fourth and fifth needles; wherein the second and third needles couple to the first knot via second and third suture lengths, and the fourth and fifth needles couple to the second knot via fourth and fifth suture lengths.

A fourteenth example includes the subject matter of example 13 comprising a second pledget, wherein (a) the first suture length is configured to pass through papillary muscle and into the second pledget to couple the first and second pledgets to the papillary muscle, and (b) the second and third suture lengths are configured to pass through valve tissue to couple the first and second suture loops to the valve tissue and provide chordal support between the papillary muscle and the valve tissue. By being so configured, for instance, the lengths of are of sufficient length to form artificial chords and/or pass from one side of papillary muscle to another side of papillary muscle. In one embodiment the lengths are such that the system may be deployed via a keyhole in the patient's chest, allowing the surgeon to push a knot (e.g., a knot between second and third suture lengths) down through the keyhole and repeat the process to "throw" 7-10 knots if the surgeon desires.

A fifteenth example includes the subject matter of any or all of examples 13-14, wherein the first suture length passes through the pledget and at least the first suture loop. In another embodiment the first suture length passes through the pledget and at least the first and second suture loops.

A sixteenth example includes the subject matter of any or all of examples 13-15, wherein the first suture loop, the first knot, and the second and third suture lengths are monolithic with one another and constitute a single suture. Such an embodiment reduces joints between two independent sutures where the joint may have diminished structural integrity (as opposed to a unit formed entirely from a single suture length).

A seventeenth example includes the subject matter of any or all of examples 13-16, wherein the second suture loop, the second knot, and the fourth and fifth suture lengths are monolithic with one another and constitute an additional single suture.

An eighteenth example includes the subject matter of any or all of examples 13-17, wherein the first and second suture loops are not monolithic with each other and do not constitute a single suture. For instance, one suture loop may be removed by a surgeon without adversely affecting the integrity of other loops. A system with 8 loops upon implantation to a patient may be trimmed to 1, 2, 3, 4 or more loops by the surgeon if the surgeon believes not all 8 loops are necessary for helping the patient.

A nineteenth example includes the subject matter of any or all of examples 13-18, wherein the first and second knots are adjustable and the first suture loop has an adjustable length based on the first knot being adjustable. For instance, a slip knot may be adjusted and thereby allow a loop to expand or contract.

A twentieth example includes the subject matter of any or all of examples 13-19, wherein the first and second knots are not adjustable and are fixed and the first suture loop has a fixed length based on the first knot being fixed.

A twenty-first example includes the subject matter of any or all of examples 13-20, wherein at least one additional suture loop is coupled between the first suture loop and the second and third needles. For instance, in FIG. 1 a fine adjustment loop is between a loop and a gross adjustment loop. Embodiments may include an embodiment such as the embodiment of FIG. 12A modified to include an additional loop between the knot 1231 and lengths 1203', 1204'. In an embodiment, any of loop members 1203, 1204, 1205, 1206 of FIG. 12B may be replaced with loop ladders such as any of the ladders of FIGS. 1-4.

A twenty-second example includes a chordal replacement method comprising: securing a pledget, which is coupled to a first suture length and at least one of a first needle and a first ferrule, to papillary muscle based on passing the first needle through the papillary muscle; securing a second suture length, which is coupled to the pledget and at least a second needle, to valve tissue based on passing the second needle through the valve tissue; and securing a third suture length, which is coupled to the pledget and at least a third needle, to the valve tissue based on passing the third needle through the valve tissue; wherein the second and third suture lengths are not monolithic with each other and do not constitute a single suture.

A twenty-third example includes the subject matter of example 22 wherein the second suture length couples to a fourth needle and the third suture length couples to a fifth needle, the method further comprising: securing the second suture length to the valve tissue by passing the fourth needle through the valve tissue; and securing the third suture length to the valve tissue by passing the fifth needle through the valve tissue.

A twenty-fourth example includes the subject matter of any or all of examples 22-23 wherein the second suture length includes a loop that is formed without any knots.

A twenty-fifth example includes the subject matter of any or all of examples 22-24, wherein the second suture length couples to a fourth needle at one end of the second suture length and couples to the second needle at another end of the second suture length, the method further comprising: securing the second suture length to the valve tissue by passing the fourth needle through the valve tissue and then coupling the one end to the another end via at least one of a knot and a coupling member.

While the present invention has been described with respect to a limited number of embodiments, those skilled in the art will appreciate numerous modifications and variations therefrom. It is intended that the appended claims cover all such modifications and variations as fall within the true spirit and scope of this present invention.

What is claimed is:

1. A chordal replacement system comprising:
first needles attached to opposing ends of a monolithic first suture, second needles attached to opposing ends of a monolithic second suture, and third needles attached to opposing ends of a monolithic third suture, wherein the first suture is not monolithic with either of the second and third sutures;
a pledget having opposing first and second sidewalls;
wherein (a) the first suture is configurable to form a first suture loop, (b) the second suture is knotted to form a second suture loop that directly connects to the second sidewall, and (c) the third suture is knotted to form a third suture loop that directly connects to the second sidewall;
wherein neither of the second or third suture loops passes through the pledget;
wherein the first sidewall directly contacts the first suture;
wherein: (a) the second suture loop and a knot of the second suture are monolithic with one another and constitute a single suture, and (b) the knot of the second suture couples the second suture loop to the second needles.

2. The system of claim 1 comprising an additional pledget, wherein: (a) the first suture is configured to pass through papillary muscle and into the additional pledget to couple both the pledget and the additional pledget to the papillary muscle, and (b) the second and third sutures are configured to pass through valve tissue to couple the second and third suture loops to the valve tissue and provide chordal support between the papillary muscle and the valve tissue.

3. The system of claim 1, wherein the first suture passes through the pledget and at least the second suture loop.

4. The system of claim 1, wherein the second and third suture loops are not monolithic with each other and do not constitute a single suture.

5. The system of claim 1, wherein the knot of the second suture and a knot of the third suture are both adjustable and the second suture loop has an adjustable length based on the knot of the second suture being adjustable.

6. The system of claim 1, wherein the knot of the second suture and a knot of the third suture are both not adjustable and are fixed and the second suture loop has a fixed length based on the knot of the second suture being fixed.

7. The system of claim 1, wherein the knot of the second suture is adjustable and the second suture loop has an adjustable length based on the knot of the second suture being adjustable.

8. The system of claim 1, wherein the knot of the second suture is not adjustable and is fixed and the second suture loop has a fixed length based on the knot of the second suture being fixed.

9. The system of claim 1, wherein at least one additional suture loop is coupled between the second suture loop and the second needles.

10. A chordal replacement system comprising:
first needles connected to opposing ends of a monolithic first suture, second needles connected to opposing ends of a monolithic second suture, and third needles connected to opposing ends of a monolithic third suture, wherein the first suture is not monolithic with either of the second and third sutures;
a pledget having opposing first and second sidewalls;
wherein (a) the first suture is configurable to form a first suture loop, (b) the second suture is knotted, via a knot of the second suture, to form a second suture loop connected to the second sidewall, and (c) the third suture is knotted, via a knot of the third suture, to form a third suture loop connected to the second sidewall;
wherein the first sidewall is connected to the first suture;
wherein the first suture passes through the pledget;
wherein: (a) the second suture loop and the knot of the second suture are monolithic with one another, and (b) the knot of the second suture couples the second suture loop to the second needles;
wherein the second and third suture loops are not monolithic with each other.

11. The system of claim 10 wherein the second and third sutures are configured to pass through valve tissue to couple the second and third suture loops to the valve tissue and provide chordal support between papillary muscle and the valve tissue.

12. The system of claim 11 comprising an additional pledget, wherein the first suture is configured to pass through the papillary muscle and into the additional pledget to couple both the pledget and the additional pledget to the papillary muscle.

13. The system of claim 12, wherein the knot of the second suture and the knot of the third suture are both adjustable and the second suture loop has an adjustable length based on the knot of the second suture being adjustable.

14. The system of claim 12, wherein the knot of the second suture and the knot of the third suture are both non-adjustable and are fixed and the second suture loop has a fixed length based on the knot of the second suture being fixed.

15. The system of claim 12, wherein the knot of the second suture is adjustable and the second suture loop has an adjustable length based on the knot of the second suture being adjustable.

16. The system of claim 12, wherein the knot of the second suture is non-adjustable and fixed and the second suture loop has a fixed length based on the knot of the second suture being fixed.

17. The system of claim 12, wherein at least one additional suture loop is coupled between the second suture loop and the second needles.

18. The system of claim 12, wherein neither of the second or third suture loops passes through the pledget.

19. The system of claim 12, wherein the first suture passes through the second suture loop.

* * * * *